(12) United States Patent
Kane et al.

(10) Patent No.: US 11,491,338 B2
(45) Date of Patent: Nov. 8, 2022

(54) POLYMERIC FEED-THRU FOR CHRONIC IMPLANTABLE DEVICES

(71) Applicant: Cardiac Pacemakers, Inc., St Paul, MN (US)

(72) Inventors: Michael J. Kane, Roseville, MN (US); Joseph T. Delaney, Jr., Minneapolis, MN (US); Kasyap Seethamraju, Eden Prairie, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 129 days.

(21) Appl. No.: 16/206,826

(22) Filed: Nov. 30, 2018

(65) Prior Publication Data

US 2019/0126052 A1    May 2, 2019

Related U.S. Application Data

(62) Division of application No. 14/790,238, filed on Jul. 2, 2015, now abandoned.

(Continued)

(51) Int. Cl.
*A61N 1/375* (2006.01)
*H01B 3/44* (2006.01)
(Continued)

(52) U.S. Cl.
CPC ............ *A61N 1/3754* (2013.01); *B32B 15/06* (2013.01); *B32B 37/12* (2013.01); *H01B 3/441* (2013.01);

(Continued)

(58) Field of Classification Search
CPC ........ A61N 1/3754; A61N 1/362; H01B 3/28; H01B 3/441; B32B 9/043; B32B 15/06;
(Continued)

(56) References Cited

U.S. PATENT DOCUMENTS 3,824,217 A * 7/1974 Barker ............... C08G 18/8058
528/59
4,367,503 A   1/1983 Treseder
(Continued)

FOREIGN PATENT DOCUMENTS

CN    102573940 A    7/2012
CN    106659895 A    5/2017
(Continued)

OTHER PUBLICATIONS

Huntsman Polyurethanes Product Line Catalog, Dec. 2013, p. 6.*
(Continued)

*Primary Examiner* — Philip C Tucker
*Assistant Examiner* — Jimmy R Smith, Jr.
(74) *Attorney, Agent, or Firm* — Nelson Mullins Riley & Scarborough LLP

(57) ABSTRACT

A method of making a feed-thru connector assembly includes inserting a conductor within an opening within a housing of a pulse generator and dispensing a sealant in a gap between the conductor and portions of the housing adjacent to the conductor that define the opening of the housing and curing the sealant to form a seal comprising a polyisobutylene cross-linked network.

12 Claims, 10 Drawing Sheets

Related U.S. Application Data

(60) Provisional application No. 62/023,648, filed on Jul. 11, 2014.

(51) Int. Cl.
  *B32B 15/06* (2006.01)
  *B32B 37/12* (2006.01)
  *A61N 1/362* (2006.01)
  *H01B 3/28* (2006.01)

(52) U.S. Cl.
  CPC ........... *A61N 1/362* (2013.01); *B32B 2457/04* (2013.01); *B32B 2581/00* (2013.01); *H01B 3/28* (2013.01)

(58) Field of Classification Search
  CPC .. B32B 37/12; B32B 2581/00; B32B 2457/04
  See application file for complete search history.

(56) References Cited

U.S. PATENT DOCUMENTS

| | | |
|---|---|---|
| 4,479,168 A | 10/1984 | Green, Jr. |
| 4,632,507 A | 12/1986 | Mignien et al. |
| 6,096,413 A * | 8/2000 | Kalinoski ............ H05K 9/0015 174/370 |
| 6,268,451 B1 | 7/2001 | Faust et al. |
| 6,903,268 B2 | 6/2005 | Marshall et al. |
| 7,164,572 B1 * | 1/2007 | Burdon ................ A61N 1/3754 361/302 |
| 7,715,922 B1 | 5/2010 | Tan |
| 8,374,704 B2 | 2/2013 | Desai et al. |
| 8,660,663 B2 | 2/2014 | Wolf et al. |
| 8,674,239 B2 * | 3/2014 | Pretzlaff .................. H01G 9/10 174/650 |
| 9,398,901 B2 | 7/2016 | Tischendorf et al. |
| 2003/0164222 A1* | 9/2003 | Kneafsey ................ C09J 9/005 401/55 |
| 2005/0092507 A1 | 5/2005 | Marshall et al. |
| 2006/0009813 A1 | 1/2006 | Taylor et al. |
| 2006/0167183 A1* | 7/2006 | Ouhadi .............. C09J 123/0892 525/192 |
| 2009/0017310 A1* | 1/2009 | Demmig ............ C08G 18/0823 428/423.1 |
| 2009/0054949 A1 | 2/2009 | Alexander et al. |
| 2009/0259265 A1 | 10/2009 | Stevenson et al. |
| 2010/0075018 A1* | 3/2010 | Desai ........................ B05D 5/08 427/2.1 |
| 2011/0031698 A1 | 2/2011 | Tziviskos |
| 2011/0045030 A1* | 2/2011 | Desai ..................... A61L 31/16 424/400 |
| 2011/0054581 A1 | 3/2011 | Desai et al. |
| 2011/0190833 A1 | 8/2011 | Ries et al. |
| 2013/0184797 A1 | 7/2013 | Tang et al. |
| 2014/0194963 A1 | 7/2014 | Desai et al. |
| 2015/0259465 A1* | 9/2015 | Burckhardt ........... C04B 40/065 524/839 |
| 2016/0008607 A1 | 1/2016 | Kane et al. |
| 2016/0122464 A1 | 5/2016 | Seppala et al. |

FOREIGN PATENT DOCUMENTS

| | | |
|---|---|---|
| JP | 2008505731 A | 2/2008 |
| JP | 2013502495 A | 1/2013 |
| JP | 2017521163 A | 8/2017 |
| WO | 2007/118117 A2 | 10/2007 |
| WO | 2008016384 A2 | 2/2008 |
| WO | 2011022583 A1 | 2/2011 |
| WO | 2016007367 A1 | 1/2016 |

OTHER PUBLICATIONS

Suprasec 9611 1K MDI Primer Overview, 2019, downloaded Apr. 12, 2021.*

The Chemistry of Polyurethane Coatings: A General Reference Manual, Mobay Corporation, 1988, p. 14.*

International Preliminary Report on Patentability issued in PCT/US2015/038959, dated Jan. 26, 2017, 7 pages.

International Search Report issued in PCT/US2015/038959, dated Sep. 16, 2015, 4 pages.

Written Opinion issued in PCT/US2015/038959, dated Sep. 16, 2015, 5 pages.

* cited by examiner

POLYMERIC FEED-THRU FOR CHRONIC IMPLANTABLE DEVICES

CROSS-REFERENCE TO RELATED APPLICATION

This application is a division of U.S. application Ser. No. 14/790,238, filed Jul. 2, 2015, which claims priority under 35 U.S.C. § 119 to U.S. Provisional Application No. 62/023,648, filed Jul. 11, 2014, which is herein incorporated by reference in its entirety.

TECHNICAL FIELD

The present invention relates to implantable pulse generators used for chronic implantable devices. More specifically, the invention relates to electrical feed-thru structures and methods for forming feed-thru structures.

BACKGROUND

This invention relates to electrical feed-thru structures, particularly for use in implantable pulse generators (IPG) such as heart pacemakers, defibrillators, and/or neuromodulation devices. It is desirable that the electrical feed-thru structures are hermetic, corrosion resistant, and impervious to body fluids.

Generally, the electrical feed-thru structure for the IPG can be made from precious metals, such as titanium, and/or high-precision machined ceramic components. The electrical feed-thru structures typically include an alumina insulator through which an electrical lead passes. The electrical lead may be brazed to the alumina insulator with a precious metal, such as gold. Insulators may also be brazed to a titanium or niobium ferrule with the precious metal. There continues to be a need to find alternative and more readily available materials for electrical feed-thru structures.

SUMMARY

Disclosed herein are various embodiments of feed-thru structures and methods for making the feed-thru structures.

In Example 1, a method of making a feed-thru connector assembly includes inserting a conductor within an opening within a housing of a pulse generator and dispensing a sealant in a gap between the conductor and portions of the housing adjacent to the conductor that define the opening of the housing and curing the sealant to form a seal comprising a polyisobutylene cross-linked network.

In Example 2, the method according to Example 1, further comprising plasma treating at least a portion of a surface of the conductor that is bonded to the seal.

In Example 3, the method according to either Example 1 or 2, further comprising priming at least a portion of the conductor with a primer comprising an epoxy functional silane or a methylene diphenyl diisocyanate (MDI).

In Example 4, the method according to any of Examples 1-3, further comprising forming the polyisobutylene cross-linked network that comprises reacting a telechelic polyisobutylene diol and a diisocyanate to form a diisocyanate derivative and reacting the diisocyanate derivative with a crosslinking initiator to form the polyisobutylene cross-linked network.

In Example 5, the method according to Example 4, wherein the diisocyanate is 4,4'-methylenephenyl diisocyanate (MDI) and the crosslinking initiator is pentaerythritol.

In Example 6, the method according to any of Examples 1-3, further comprising forming the polyisobutylene cross-linked network that comprises reacting a diisocyanate with a polyol or a polyamine to form a polyisocyanate and reacting the polyisocyanate with a telechelic polyisobutylene diol to form the polyisobutylene cross-linked network.

In Example 7, the method according to Example 6, wherein the diisocyanate comprises 4,4'-methylenephenyl diisocyanate (MDI) and the polyol comprises 1,1,2,2-Tetrakis(p-hydroxyphenyl)ethane.

In Example 8, the method according to any of Examples 1-3, further comprising forming a polyisobutylene cross-linked network by reacting together a telechelic polyisobutylene derivative, a silane agent and a transition metal species.

In Example 9, the method according to Example 8, wherein the telechelic polyisobutylene derivative is a telechelic polyisobutylene dichloride or a telechelic polyisobutylene diallyl.

In Example 10, the method according to any of Examples 8-9, wherein the silane agent has more than two reactive hydrosilane groups per molecule in the presence of a catalyst.

In Example 11, the method according to any of Examples 8-9, wherein the silane agent is a phenylsilane.

In Example 12, the method according to any of Examples 8-11, wherein the transition metal catalyst activates vinyl groups of the telechelic polyisobutylene derivative to form crosslink bridges between the telechelic polyisobutylene derivative and the silane agent.

In Example 13, the method according to any of Examples 1-3, further comprising forming a polyisobutylene cross-linked network by reacting together a polyisobutylene diallyl and a thiol-ene.

In Example 14, a feed-thru connector assembly positioned at least partially within an opening in a pulse generator housing includes a conductor disposed within the opening of the pulse generator housing and a seal disposed within a gap between the conductor and portions of the pulse generator housing adjacent to the conductor, wherein the seal comprises a polyisobutylene cross-linked network.

In Example 15, the feed-thru connector assembly according to Example 14, wherein the seal has a leak test rate less than about $4 \times 10^{-9}$ atm cc/sec (or Pa m$^3$/s) when subjected to helium gas at a pressure of about 0.4 Pa.

In Example 16, an implantable system includes a pulse generator including a housing, electronics within the housing, and an opening, a lead attached to the pulse generator, a feed-thru connector assembly mounted on the pulse generator and positioned at least partially within the opening. The feed-thru connector assembly comprises a conductor and a seal disposed within a gap between the conductor and portions of the housing adjacent to the conductor that define the opening of the housing, wherein the seal comprises a polyisobutylene cross-linked network.

In Example 17, the implantable system according to Example 16, wherein the conductor comprises one of titanium, platinum iridium (PtIr), palladium iridium (PdIr), stainless steel SS316, MP35N, silver and gold alloys, and mixtures thereof.

In Example 18, the implantable system according to Examples 16 and 17, wherein at least a portion of a surface of the conductor includes a roughened surface.

In Example 19, the implantable system according to any of Examples 16-18, wherein the tensile strength between the conductor and the seal is greater than 1,500 psi.

In Example 20, the implantable system according to any of Examples 16-19, wherein the seal has a leak test rate less than about $4 \times 10^{-9}$ atm cc/sec when subjected to helium gas at a pressure of about 0.4 Pa In Example 21, the implantable system according to any of Examples 16-20, wherein the dielectric strength of the seal is greater than 1000 volts per mil.

In Example 22, the implantable system according to any of Examples 16-21, wherein the bulk resistivity of the seal is greater than $1 \times 10^7$ ohm-m.

In Example 23, the implantable system according to any of Examples 16-22, wherein the surface resistivity of the seal is greater than $1 \times 10^6$ ohm-m.

In Example 24, a method of making a feed-thru connector assembly for a pulse generator includes inserting a conductor within an opening within a housing of the pulse generator, the conductor being coupled to electronics housed within the housing, dispensing a sealant in a gap between the conductor and portions of the housing adjacent to the conductor that define the opening of the housing and curing the sealant to form a seal comprising a polyisobutylene cross-linked network, wherein the seal is adapted to create a hermetic seal for the feedback assembly portion.

In Example 25, the method according to Example 24, further comprising plasma treating at least a portion of the surface of the conductor that is bonded to the seal.

In Example 26, the method according to Example 24 or 25, further comprising priming at least a portion of the conductor with a primer comprising an epoxy functional silane or a methylene diphenyl diisocyanate (MDI).

In Example 27, the method according to any of Examples 24-26, further comprising forming the polyisobutylene cross-linked network that comprises reacting a telechelic polyisobutylene diol and a diisocyanate to form a diisocyanate derivative and reacting the diisocyanate derivative with a crosslinking initiator to form the polyisobutylene cross-linked network.

In Example 28, the method according to any of Examples 24-27, wherein the diisocyanate is 4,4'-methylenephenyl diisocyanate (MDI) and the crosslinking initiator is pentaerythritol.

In Example 29, the method according to any of Examples 24-26, further comprising forming the polyisobutylene cross-linked network that comprises reacting a diisocyanate with a polyol or a polyamine to form a polyisocyanate and reacting the polyisocyanate with a telechelic polyisobutylene diol to form the polyisobutylene cross-linked network.

In Example 30, the method according to Example 29, wherein the diisocyanate comprises 4,4'-methylenephenyl diisocyanate (MDI) and the polyol comprises 1,1,2,2-Tetrakis(p-hydroxyphenyl)ethane.

In Example 31, the method according to any of Examples 24-26, further comprising forming a polyisobutylene cross-linked network by reacting together a telechelic polyisobutylene derivative, a silane agent and a transition metal species.

In Example 32, the method according to Example 31, wherein the telechelic polyisobutylene derivative is a polyisobutylene dichloride or a polyisobutylene diallyl.

In Example 33, the method according to Example 31, wherein the silane agent has more than two reactive hydrosilane groups per molecule in the presence of a catalyst.

In Example 34, the method according to Example 31, wherein the silane agent is a phenylsilane.

In Example 35, the method according to Example 31, wherein the transition metal catalyst activates vinyl groups of the telechelic polyisobutylene derivative to form crosslink bridges between the telechelic polyisobutylene derivative and the silane agent.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
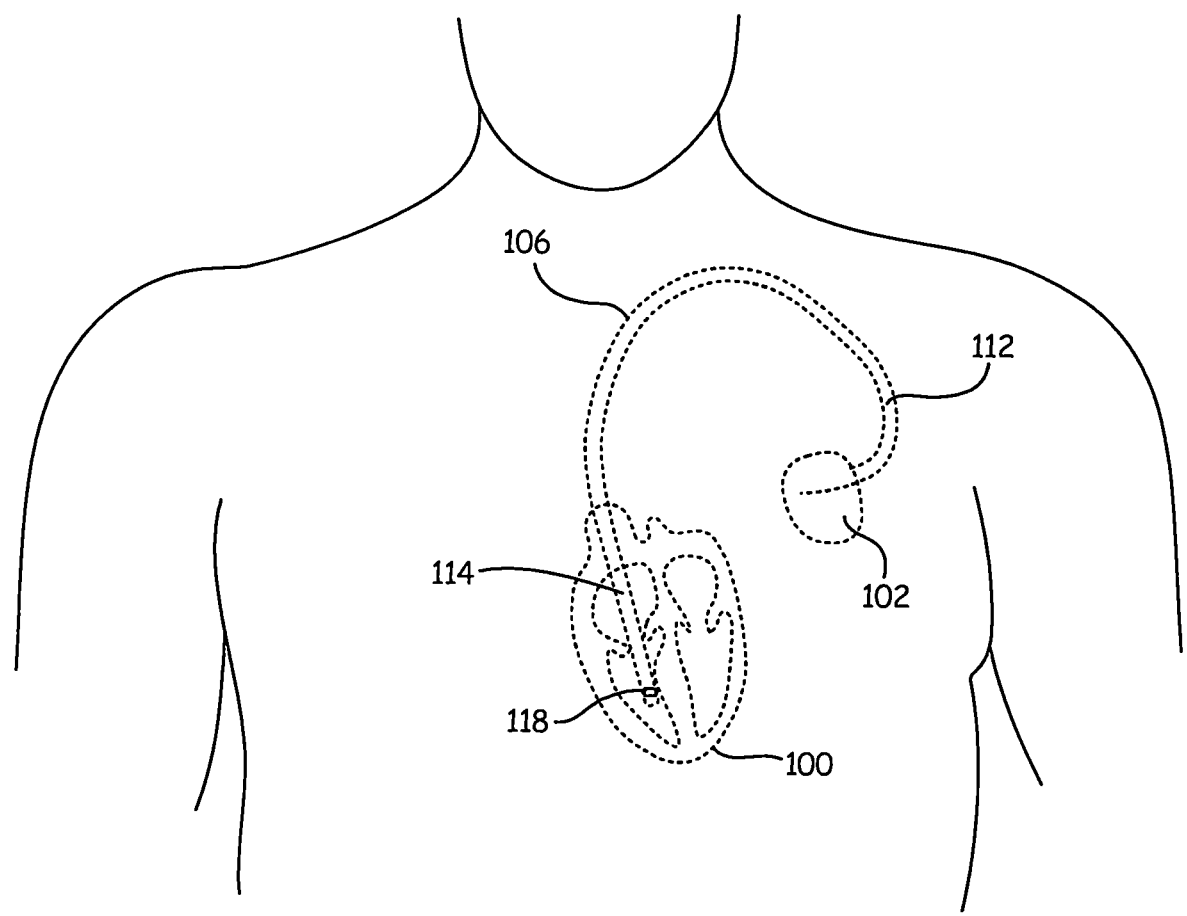
FIG. 1 is a schematic illustration of an implantable system implanted within a patient that delivers electrical simulation to the heart according to various embodiments of the invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic illustration of an implantable system within a patient that delivers electrical simulation to the heart. Although FIG. 1 is shown delivering electrical simulation to the heart, embodiments of the present disclosure can also be used in devices where electrical stimulation is provided to other areas, for example, spinal cord stimulation, as well as subcutaneous electrode configurations. The embodiment of FIG. 1 shows that the implantable system includes a pulse generator 102 arranged for producing electrical stimulation for the heart 100. In some embodiments, pulse generators can be heart pacemakers, defibrillators, and/or neuromodulation devices. The pulse generator 102 is typically implanted subcutaneously within an implantation location or pocket in the patient's chest or abdomen. The pulse generator 102 is connected to an implantable lead 106. The lead 106 operates to convey electrical signals between the implantable pulse generator 102 and the heart 100. The lead 106 includes a flexible lead body having a proximal end portion 112 and a distal end portion 114. In various embodiments, the lead 106 enters the vascular system through a vascular entry site formed in the wall of the left subclavian vein. Other suitable vascular access sites may be utilized in various other embodiments. The lead 106 can extend through the left brachiocephalic vein and the superior vena cava such that one or more electrodes 118 disposed on the distal end portion 114 of the lead 106 can be implanted in the right atrium, right ventricle, left ventricle, or other location.

Figure 2:
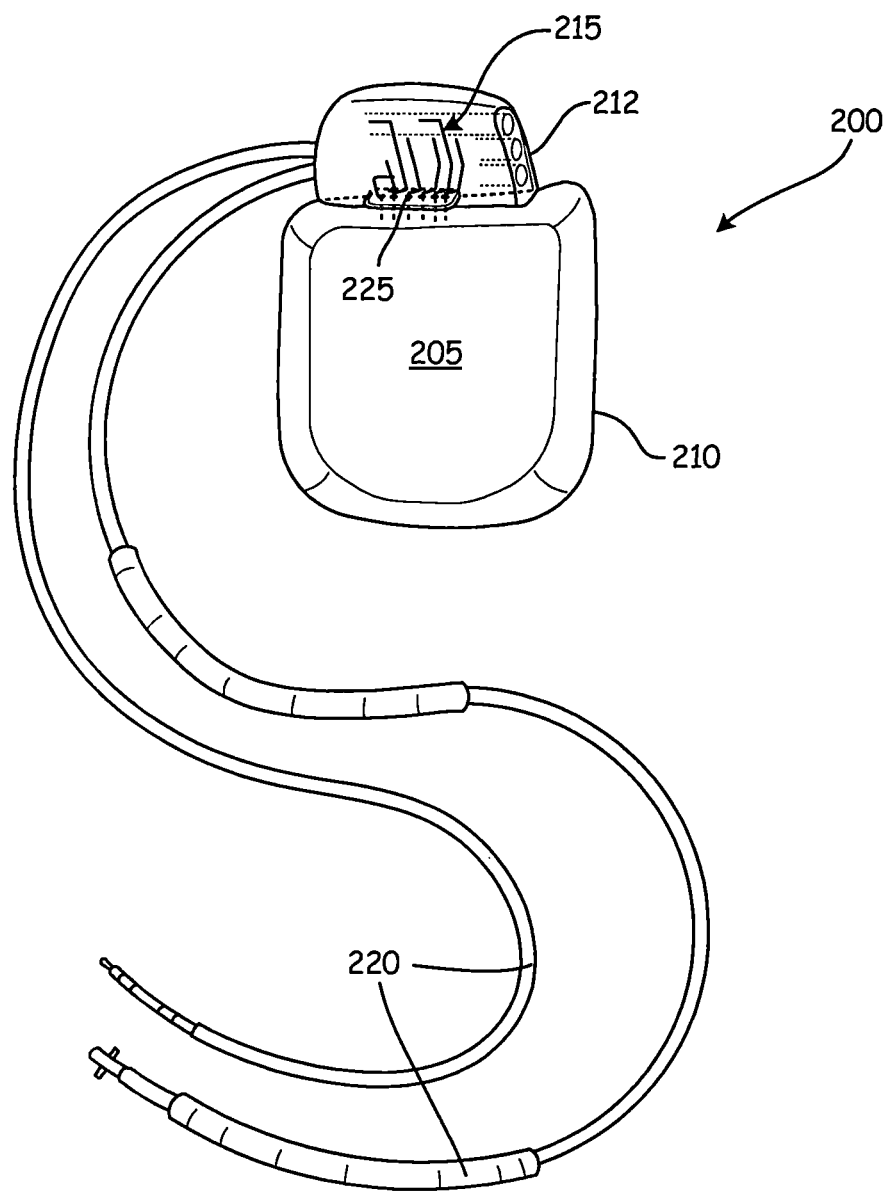
FIG. 2 is a schematic illustration of the implantable system of FIG. 1 with a partial cross-sectional view of a pulse generator according to various embodiments of the invention.

FIG. 2 provides a schematic illustration of an implantable system 200 with a partial cross-sectional view of a pulse generator 205 according to various embodiments. The pulse generator 205 includes a pulse generator housing 210 comprising electronics (not shown), a battery power source (not shown), and a header 212 mounted on an exterior portion of the pulse generator housing 210. The pulse generator housing 210 includes a feed-thru structure, e.g., a feed-thru connector assembly 215, which operatively couples the implantable lead 220, when connected, to the electronics within the pulse generator 205. The pulse generator housing 210 includes an opening 225, according to some embodiments. In some embodiments, the housing 210 may include a plurality of openings 225. The pulse generator housing 210 can be machined, molded or otherwise formed from a biocompatible metal. In some embodiments, the pulse generator housing 210 is made of titanium, titanium alloy, MP35N, stainless steel or combinations thereof.

The feed-thru connector assembly 215, in various embodiments, seals the opening 225 of the pulse generator 205. As such, the feed-thru connector assembly 215 hermetically seals the interior cavity of the pulse generator 205 from the external environment, e.g., sealing the interior cavity from moisture and/or biologics. The feed-thru connector assembly 215 can include various sealing materials. In some embodiments, at least a portion of the feed-thru connector assembly 215 is made of a material having low vapor permeability characteristics. The feed-thru connector assembly 215 seals the opening 225 of the pulse generator 205 such that the header 212 can be made of a material with a higher permeability characteristic than a sealing material of the feed-thru connector assembly 215, in some embodiments.

As shown in FIG. 2, the header 212 may be mounted on at least a portion of the pulse generator housing 210. In some embodiments, the header 212 is disposed over a portion of the pulse generator housing 210 comprising the feed-thru connector assembly 215. The header 212 may provide structural integrity to the feed-thru connector assembly 215 by comprising a material having suitable mechanical strength characteristics. The header 212 may also reinforce the bond between the feed-thru connector assembly 215 and the pulse generator housing 210. In some embodiments, the header 212 provides a material barrier between the feed-thru connector assembly 215 and an external environment such that the feed-thru connector assembly 215 is no longer in direct patient contact during device use.

Suitable materials for the header 212 may include various biocompatible metals, polymers, ceramics or combinations thereof. In various embodiments, the header 212 is made of an insulative material. In some embodiments, the header 212 is made of a thermoset or a thermoplastic polymer. Examples of materials that may be used for the header 212 include, but are not limited to, epoxy, polyurethane, polytetrafluoroethylene (PTFE), polycarbonate, polyetheretherketone (PEEK), stainless steel, high density polyethylene (HDPE), polypropylene (PP), polyvinyl chloride (PVC), nylon, ferrous and non-ferrous metals or metal alloys, composites or combinations thereof.

Figure 3:
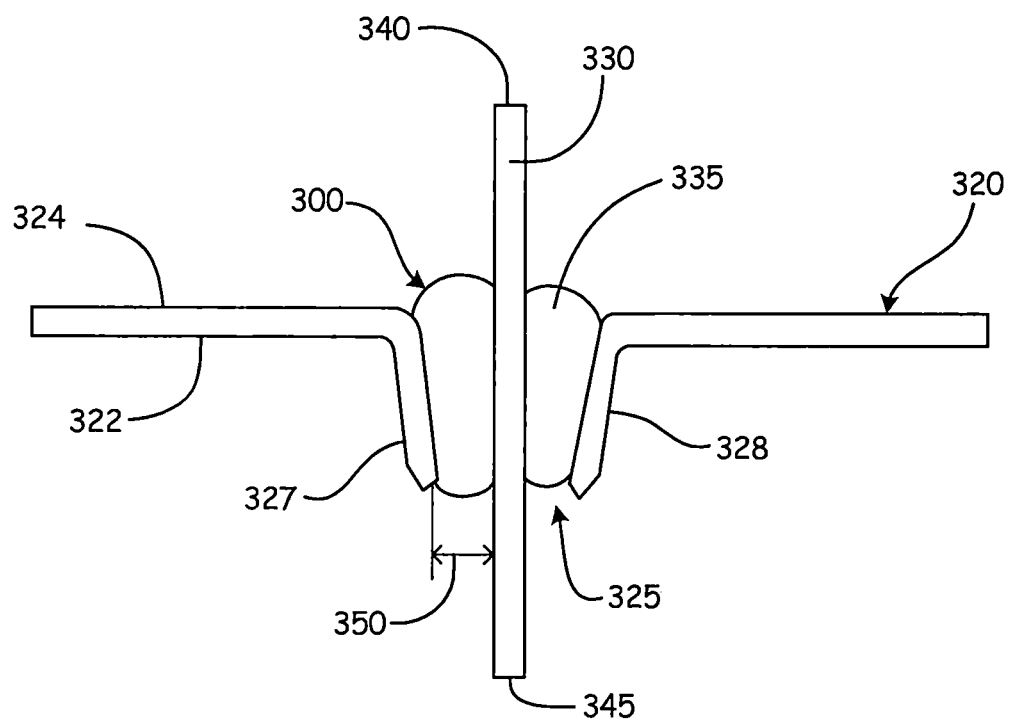
FIGS. 3-6 are cross-sectional views of a feed-thru structure according to various embodiments of the invention.

FIG. 3 is a cross-sectional view of a feed-thru connector assembly 300 according to various embodiments. As shown, a pulse generator housing 320 includes an interior surface 322, an exterior surface 324, and an opening 325 defined by first and second walls 327, 328. In FIG. 3, at least a portion of the feed-thru connector assembly 300 is positioned at least partially within the opening 325 and conforms in shape to an area extending between the first and second walls 327, 328 of the housing 320.

The opening 325 may have any suitable cross-sectional shape. In some embodiments, the opening 325 may have a circular cross-sectional shape such that the first and second walls 327, 328 are a single, continuous wall. The opening 325 may be of any suitable size. The opening 325 may be sized to enable the wire 330 to pass through or extend axially through the opening 325. In some embodiments, the opening 325 may be sized to enable more than one wire 330 to pass from a location outside of the pulse generator housing 320 to a location inside of the pulse generator housing 320. The opening 325 can be formed by deforming a portion of the pulse generator housing 320. For example, in some embodiments, the opening is formed by punching, stamping or drawing at least a portion of the housing 320. In some embodiments, the pulse generator housing 320 is deformed such that a portion of the housing 320 adjacent the opening forms a flared portion (not shown) that extends outwardly from the exterior surface 324 of the pulse generator housing 320. The flared portion is a structural feature that can interact with the header material to create a mechanical bond that improves the bond between the header and the pulse generator housing 320.

The feed-thru connector assembly 300 can include a conductor disposed at least partially within the opening 325 and through a seal 335. As shown in FIG. 3, for example, the conductor can be a wire 330 disposed within the opening 325. Other examples of suitable conductor types, in some embodiments, include a ribbon, a filament, and any rod with a polygonal shaped cross-section, such as a triangular or a hexagonal cross-section.

The wire 330 can be positioned within the opening 325 of the pulse generator housing 320. In some embodiments, the wire 330 is positioned such that a portion of the wire 330 is located external to the pulse generator housing 320 and a portion of the wire 330 is located internally within the pulse generator housing 320. For example, the wire 330 may be oriented such that a proximal end 340 of the wire 330 extends outwardly from the opening 325 and a distal end 345 extends into an inner cavity of the pulse generator housing 320. The feed-thru connector assembly 300 allows the implantable lead 220 to be coupled to electronics and a source battery within the pulse generator 205 (FIG. 2) through the wire 330.

The wire 330 extends through the opening 325 and the seal 335 is positioned between the wire 330 and first and second walls 327, 328. The wire 330 may be also described as a feed-thru wire, a pin or a conductor. In some embodiments, the wire 330 may be straight (that is, the distal and proximate ends of the wire 330 may axially align). The wire 330 may be operatively connected either directly or indirectly to electronics (FIG. 7), e.g., a printed circuit board or other electronic components, within the pulse generator housing 320. In some embodiments, the wire 330 is fixed directly to the printed circuit board or the other electronic components. In some embodiments, the wire 330 may be soldered, wire-bonded or welded to the printed circuit board or the other electronic components.

The wire 330 is made of a metallic material in various embodiments. For example, in some embodiments, the wire 330 is made of titanium. The wire 330 may be formed of any suitable material, for example, titanium, tantalum, tungsten, platinum, palladium, stainless steels (e.g., SS316), nickel-cobalt-chromium-molybdenum alloys such as MP35N, MP35N/silver drawn braze strand, MP35N/silver drawn filled tube, nitinol, cobalt-chromium-nickel alloy (e.g. elgiloy), cobalt-chromium-nickel-molybdenum-iron alloys or combinations thereof. Other exemplary materials for the wire 330 include, but are not limited to, platinum iridium (PtIr), palladium iridium (PdIr), silver (Ag), gold (Au) or combinations thereof.

In some embodiments, at least a portion of a surface of the wire 330 includes at least one feature to improve the bond between the seal 335 and the wire 330. At least a portion of an exterior surface of the wire 330, for example, the portion of the wire 330 that is bonded to the seal 335, may include a roughened surface or a contoured surface (see FIG. 4). In some embodiments, the entire length of the wire 330 includes the roughened surface or contoured surface. Additionally or alternatively, the wire 330 may include at least one roll or groove feature (not shown). In some embodiments, the roll or groove feature may increase the bonding surface area of the wire 330. The roll or groove feature may create a mechanical bond between the seal 335 and the wire 330. The seal 335 of the feed-thru connector assembly 300 may conform in shape to a volumetric space and a surface profile. In some embodiments, the seal 335 can conform to a space between two adjacent components. For example, the seal 335 of the feed-thru connector assembly 300 can be disposed within a gap 350 between the wire 330 and portions of the pulse generator housing 320 adjacent to the wire 330 that define the opening 325, as shown in FIG. 3. In some embodiments, a portion of the seal 335 can be formed into a flat, uniform surface or alternatively, an irregular, non-uniform surface. In various embodiments, a sealant is disposed within the gap 350 to form the seal 335 within the feed-thru connector assembly 300. The seal 335 of the feed-thru connector assembly 300 hermetically seals and protects the interior components of the pulse generator 205 from moisture and fluids present in the external environment.

In some embodiments, the seal 335 may be exposed at the exterior surface 324 of the pulse generator housing 320 to an exterior environment, such as an exterior environment comprising human bodily fluids. Accordingly, in some embodiments, the seal 335 may made be of a biocompatible material. Suitable materials for the seal 335 include various polyisobutylene-based materials as described herein.

In various embodiments, the seal 335 comprises a polyisobutylene cross-linked network (PIB-CN) material. The seal 335 can be formed of a thermoset PIB-CN. In some embodiments, the PIB-CN seal 335 is made of a solid material that exhibits rubber-like characteristics. In some embodiments, the PIB-CN seal 335 possesses low vapor-transmission characteristics. Due to its low permeability to gases, the PIB-CN seal 335 can hermetically seal the opening 325 of the pulse generator 205.

In various embodiments, the PIB-CN seal 335 suitably bonds to a metal or metallic component, e.g. the wire 330. In some embodiments, the PIB-CN seal 335 can covalently bond to the metal or metallic component. For example, in some embodiments, the PIB-CN seal 335 may bond to the titanium oxide surface of a titanium wire. The PIB-CN seal 335, in some embodiments, bonds to an activated metallic surface, e.g., a plasma treated metallic surface.

The PIB-CN seal 335 can be bonded to the wire 330 with a suitable tensile strength. In some embodiments, the PIB-CN seal 335 may be bonded to the wire 330 with a tensile strength sufficient to hermetically seal the opening 325 of the pulse generator housing 320. In some embodiments, the PIB-CN seal 335 bonds to the metallic component, e.g. the wire 330, such that the tensile strength values between the metallic component and the PIB-CN seal 335 is greater than 1,500 pounds per square inch (psi), or 10.34 megapascals (MPa). In some embodiments, the PIB-CN seal 335 can have a suitable tensile strength range from about 30 psi to about 60 psi, or about 207 kilopascals (kPa) to about 414 kPa. Other suitable tensile strength ranges also include the range from about 60 psi (414 kPa) to about 100 psi (689 kPa), from about 100 psi (689 kPa) to 500 psi (3.45 MPa) and from about 500 psi (3.45 MPa) to about 1500 psi (10.3 Mpa), in some embodiments.

The PIB-CN seal 335 provides a thermally stable material that is capable of being stable at temperatures up to about 380° C., in some embodiments. In some embodiments, the sealant used for forming the PIB-CN seal 335 may use an extruding, dispensing, coating or dipping process when being applied between the pulse generator housing 320 and wire 330.

In various embodiments, the PIB-CN material may be formed from a telechelic PIB derivative. As used herein, the term "telechelic", means a polymer that has functionalized endgroups, and includes homo-telechelic polymers and hetero-telechelic polymers. The term "homo-telechelic" means a di-end or tri-end functional polymer where both or all ends possess the same functionality, while the term "hetero-telechelic" means a di- or tri-end functional polymer where the ends possess different functionality. Telechelic polymers can be used, e.g., for the synthesis of block co-polymers. There are various telechelic PIB derivatives that can be used to synthesize the PIB-CN material. In some embodiments, the telechelic PIB derivative is a linear block polymer, for example, a PIB-dichloride or a PIB-diallyl. Examples of the telechelic PIB derivatives include, but are not limited to, polyisobutylene dichloride (PIB-dichloride), polyisobutylene diallyl (PIB-diallyl) and polyisobutylene diol (PIB-diol). Additionally or alternatively, in some embodiments, the PIB-CN material may be formed from a non-telechelic PIB derivative that includes at least one graft or pendant group to facilitate a crosslinking reaction that produces a thermoset cross-linked network.

The telechelic PIB derivative may be synthesized from a telechelic PIB initiator, according to some embodiments. In particular, in various embodiments, the telechelic initiator is a difunctional cationic initiator that includes, but is not limited to, structures shown in Formulas 1-3.

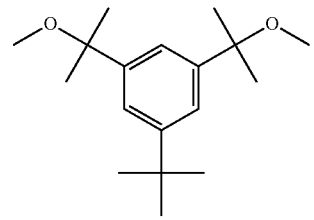

Formula 1

Structure of hindered dicumyl ether

This compound (CAS No. 108180-34-3) is known as 1-(1,1-dimethylethyl)-3,5-bis(1-methoxy-1-methylethyl)-benzene, or alternatively as 1,3-bis(2-methoxy-2-propyl)-5-tert-butylbenzene, 1,3-bis(1-methoxy-1-methylethyl)5-tert-butylbenzene or 5-tert-butyl-1,3-bis(1-methoxy-1-methylethyl)benzene. This compound is referred to herein as "hindered dicumyl ether" or HDCE. A process for forming HDCE is described in U.S. patent Ser. No. 13/748,046 filed Jan. 23, 2013 entitled Synthetic methods pertaining to tert-butylbenzene based compounds, which is incorporated herein by reference in its entirety.

A related compound that has also been used as a difunctional initiator for living cationic polymerization is shown in Formula 2.

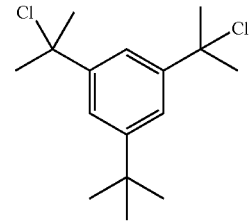

Formula 2

Structure of hindered dicumyl chloride

This compound (CAS No. 89700-89-0) is known as 1,3-bis(1-chloro-1-methylethyl)-5-(1-dimethylethyl)benzene or alternatively as 1,3-bis(1-chloro-1-methylethyl)-5-tert-butylbenzene. This compound is referred to herein as "hindered dicumyl chloride" or HDCC.

Another related compound that has been used as a difunctional initiator for polymerization is shown in Formula 3.

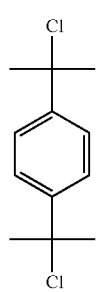

Formula 3

Structure of dicumyl chloride

This compound (CAS No. 7374-80-3) is known as 1,4-bis(2-chloropropan-2-yl)benzene, or alternatively as 1,4-bis(1-chloro-1-methylethyl)benzene. This compound is referred to herein as "dicumyl chloride" or DCC.

In various embodiments, the telechelic PIB initiator, such as HDCE, HDCC or DCC, may be used to polymerize isobutylene and form telechelic PIB derivatives. For example, in some embodiments, HDCE forms a linear PIB chain with two tertiary substituted chloride end groups, called PIB-dichloride. An exemplary reaction is shown in Scheme 1:

Scheme 1: Synthesis of PIB-dichloride.

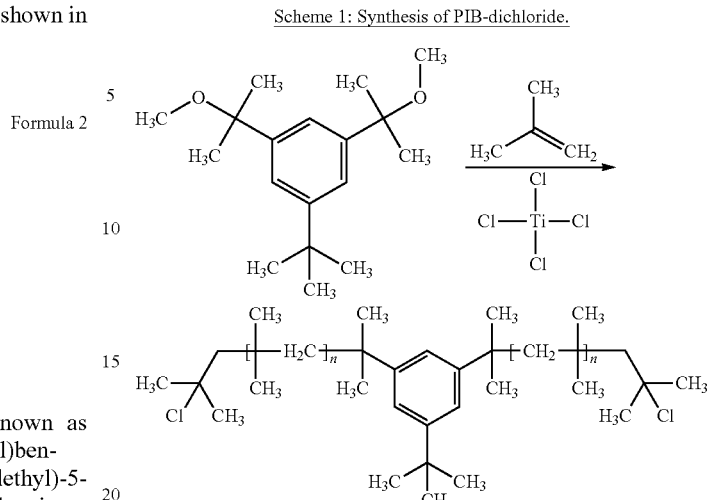

In various embodiments, the PIB-dichloride may be converted to an allyl terminated PIB-diallyl. For example, in some embodiments, PIB-dichloride is reacted with allyltrimethylsilane to produce the PIB-diallyl, as shown in Scheme 2:

Scheme 2: Synthesis of PIB-diallyl.

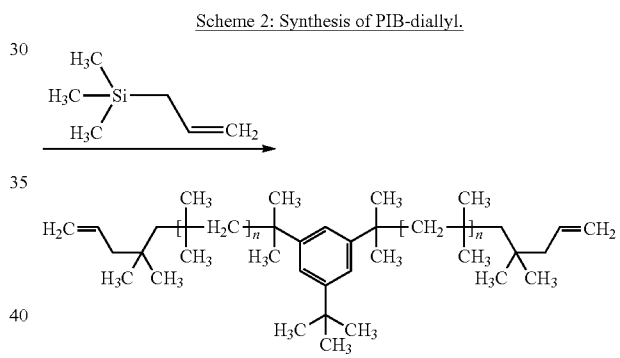

The PIB-diallyl may be further converted into a PIB-diol, according to some embodiments. For example, the PIB-diol is subjected to hydroboration with 9-Borabicyclo[3.3.1]nonane (or 9-BBN), also known as borabicyclononane, and oxidation of the intermediate using hydrogen peroxide, to form a telechelic hydroxyl, propyl terminated PIB-diol, as shown in Scheme 3.

Scheme 3: Synthesis of PIB-diol.

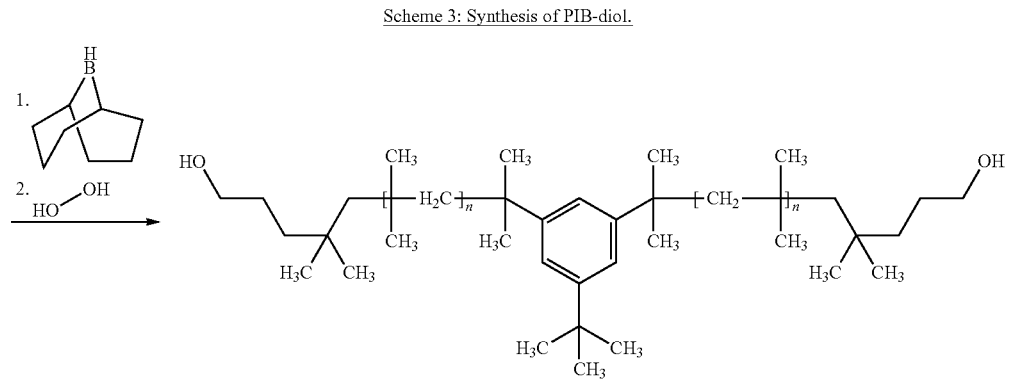

In various embodiments, at least one of the telechelic PIB derivatives, as described herein, may be used to form a thermoset PIB-CN material.

There are various suitable methods to synthesize the PIB-CN material from the telechelic PIB derivative. In some embodiments, a suitable method for producing the PIB-CN material may include using a telechelic PIB-diol reactant or a telechelic PIB-diallyl reactant in a PIB-CN synthesis reaction.

In some embodiments, a suitable method for synthesizing the PIB-CN material includes a reaction that uses a diisocyanate reactant. In various embodiments, the diisocyanate can be at least one member selected from the group consisting of 4,4'-methylenephenyl diisocyanate; methylene diisocyanate; p-phenylene diisocyanate; cis-cyclohexane-1,4-diisocyanate; trans-cyclohexane-1,4-diisocyanate; a mixture of cis-cyclohexane-1,4-diisocyanate and trans-cyclohexane-1,4-diisocyanate, 1,6-hexamethylene diisocyanate; 2,4-toluene diisocyanate; cis-2,4-toluene diisocyanate; trans-2,4-toluene diisocyanate; a mixture of cis-2,4-toluene diisocyanate and trans-2,4-toluene diisocyanate; p-tetramethylxylene diisocyanate; and m-tetramethylxylene diisocyanate.

A suitable synthesis reaction may include use of chain extenders. In some embodiments, the use of reactants in conjunction with difunctional chain extenders modify the distance of cross-linked bonds in the PIB-CN material. Difunctional chain extenders (f=2) and cross linkers (f=3 or greater) are low molecular weight hydroxyl and amine terminated compounds (e.g., compounds having a molecular weight less than 1000 g/mol) that play an important role in the polymer morphology of polyurethane-based materials. Examples of chain extenders and crosslinking initiators are ethylene glycol (EG), 1,4-butanediol (BDO), diethylene glycol (DEG), glycerine, and trimethylol propane (TMP).

In some embodiments, the chain extender can be at least one member selected from the group consisting of 1,4-butanediol (BDO); 1,5 pentanediol; 1,6-hexanediol; 1,8-octanediol; 1,9-nonanediol; 1,10-decanediol; 1,12-dodacanediol; 1,4-cyclohexane dimethanol; p-Xylene glycol; and 1,4-bis(2-hydroxyethoxy) benzene.

In some embodiments, a suitable reaction may include a diisocyanate that is a 4,4'-methylenephenyl diisocyanate and a chain extender that is a 1,4-butanediol.

There are various suitable methods to initiate crosslinking, or curing, of the PIB-CN material. In various embodiments, the PIB-CN material may be formed or cured using a crosslinking initiator, also described as a cross-linker, free radical initiator, or a curing initiator. For example, the crosslinking initiator may be reacted with a reactant or a reactive intermediate, in some embodiments.

In various embodiments, the crosslinking initiator may have more than two proton donating groups, such as an alcohol (polyol) or an amine (polyamine). In some embodiments, the crosslinking initiator may be used in a reaction for crosslinking isocyanate groups. The crosslinking initiator is a monomeric or oligomeric compound having at least two nucleophilic functional groups capable of reacting with an isocyanate group, such as —OH, —NHR with R being a H or C1-C4 alkyl, or SH, in some embodiments. In some embodiments, a reaction includes a polyol crosslinking initiator, e.g., pentaerythritol. In some embodiments, a reaction includes a polyamine crosslinking initiator, e.g., melamine or tris(2-aminoethylamine).

Crosslinking may be achieved using a wide variety of crosslinking initiators, also described as free radical initiators, such as a thermal initiator, a photoinitiator or a redox initiator. A thermal initiator is a chemical compound that decomposes and produces free radicals when subjected to heat. A photointiator is a chemical compound that produces free radicals when exposed to UV light. The crosslinking initiator may be added to the reaction when synthesizing the PIB-CN material.

In some embodiments, peroxide may be used as the crosslinking initiator. Peroxide crosslinking initiators are thermal initiators that may be prepared from alcohols, ketones, and acids. Such peroxides may also be further stabilized or derivatized through the formation of ethers, acetals, and esters. Examples of common commercially available peroxides include, but are not limited to, benzoyl peroxide, 2-butanone peroxide, t-butylperacetate, t-butylperoxide, 2,5-di(t-butylperoxy)-2,5-dimethyl-3-hexyne, dicumyl peroxide, 2,4-pentanedione peroxide, 1,1-bis(tert-butylperoxy)cyclohexane, lauroyl peroxide, and t-butylperoxy 2-ethylhexyl carbonate.

In some embodiments, an azo initiator may be used as the crosslinking initiator to cross-link the sealant. Azo initiators are thermal initiators derived from diasene and have the functional group R—N+N—R', where R and R' are either an aryl or alkyl group. Examples of azo crosslinking initiators include, but are not limited to, 2,2'-azo-bis-isobutyronitrile (AIBN), 1,1'-azobis(cyclohexanecarbonitrile), and 4,4-azo-bis(4-cyanovaleric acid).

In some embodiments, a photoinitiator may be used as the crosslinking initiator. Examples of crosslinking photoinitiators include, but are not limited to, 4-(2-hydroxyethoxy) phenyl-(2-hydroxy-2-propyl)ketone (such as Irgacure® 2959, available from BASF), benzil, benzoin, benzophenone, 2,2-dimethoxy-2-phenylacetophenone, acetophenone-based derivatives, and benzyl-based derivatives.

Various suitable methods may be used for synthesizing the PIB-CN material. In various embodiments, a one-step reaction is used to synthesize the PIB-CN material. A two-step approach, also described as a two-step reaction, is used to synthesize the PIB-CN material, in some embodiments.

A first suitable method for synthesizing the PIB-CN material includes using a two-step approach that involves (1) converting a telechelic PIB-diol to a diisocyanate derivative by exposing the PIB-diol to an excess of diisocyanate and (2) reacting the diisocyanate derivative with a crosslinking initiator to form the telechelic PIB-CN material. The telechelic PIB-diol can be converted to the diisocyanate derivative by allowing the PIB-diol to react with two equivalents of the diisocyanate, resulting in a diisocyanate end-capped PIB.

In a first step, the PIB-diol, as discussed herein, may be reacted with the diisocyanate. The various examples of the diisocyanate as discussed herein may be used in the first step reaction.

In some embodiments, the first step may include the use of organic acids as a proton donating group. In some embodiments, the organic acids may undergo further reaction via an internal rearrangement to form polyamide linkages as carbon dioxide off-gas (see W. R. Sorenson *J. Org. Chem.*, 1959, 24 (7), pp 978-980).

In the second step, the diisocyanate derivative can be reacted with the crosslinking initiator as discussed herein, e.g., such as a pentaerythritol. In various embodiments, the diisocyanate derivative is reacted with a crosslinking initiator, as discussed herein, that has more than two proton donating groups, such as alcohols (polyols) or amines (polyamines). In some embodiments, a reaction that includes a polyol crosslinking initiator can produce a polyurethane cross-linked network. In some embodiments, a reaction that includes a polyamine, e.g., melamine or tris(2-aminoethyl-amine), can produce a polyurea-urethane network.

As described herein, in some embodiments, the synthesis includes (1) converting the telechelic PIB derivative to the diisocyanate derivative and subsequently (2) crosslinking the diisocyanate derivative with the crosslinking initiator, as discussed herein, to form the PIB-CN material. For example, in some embodiments, the PIB-diol may be reacted with 4,4'-methylenephenyl diisocyanate (MDI) to produce the diisocyanate derivative in the first step.

Figure 9A:
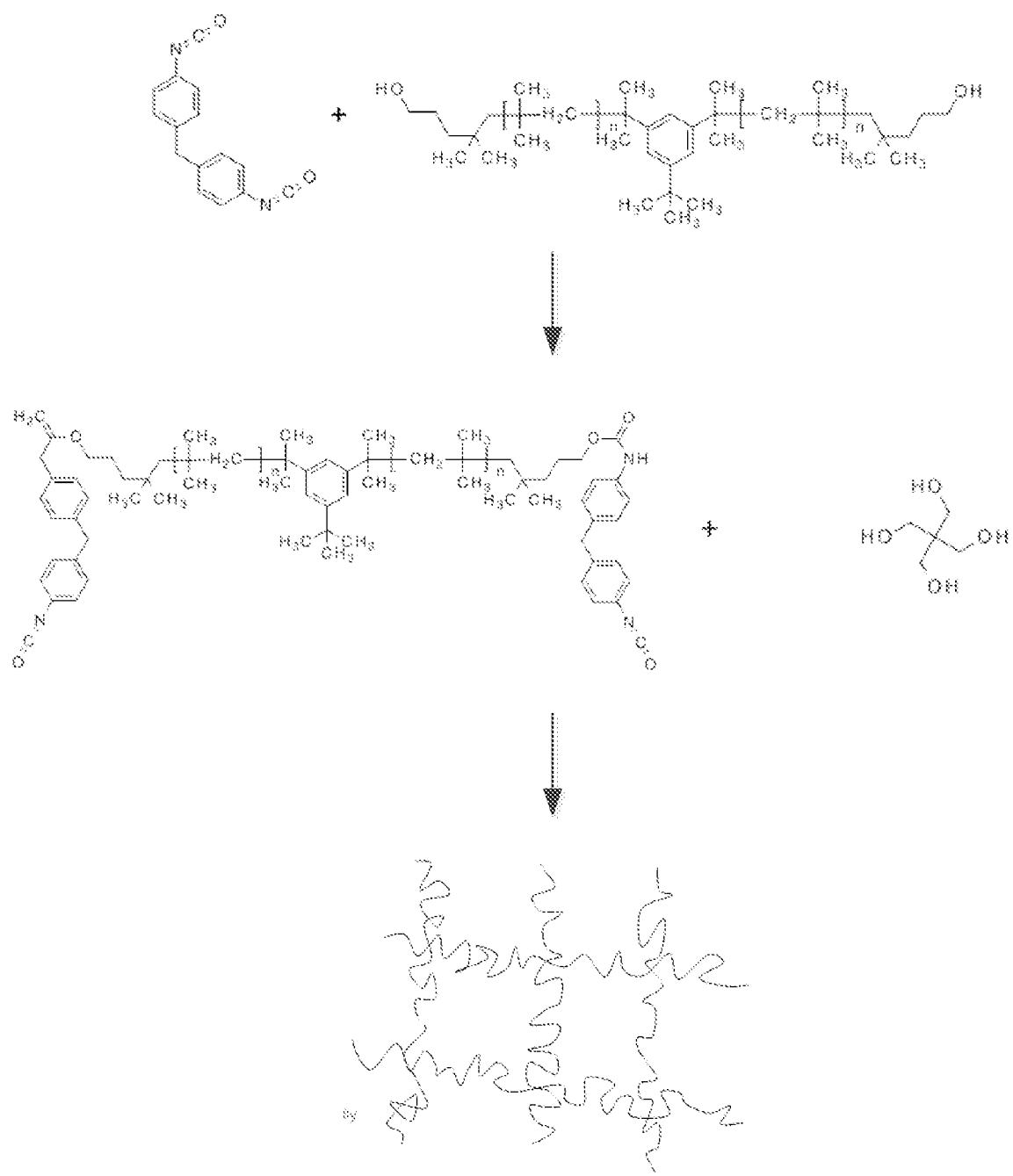
FIG. 9A shows synthesis of PIB-CN based on a PIB to a polyurea-urethane network reaction.

An exemplary synthetic path for producing the PIB-CN material is shown in FIG. 9A (Scheme 4). As shown in FIG. 9A, the telechelic PIB-diol and the diisocyanate first form the diisocyanate derivative, which is subsequently reacted with the crosslinking initiator to form the telechelic PIB-CN material. In particular, the exemplary synthesis converts the telechelic PIB derivative to the diisocyanate derivative and subsequently (2) crosslinks the diisocyanate derivative with the crosslinking initiator to form the PIB-CN material. More specifically, as shown, the PIB-diol is reacted with 4,4'-methylenephenyl diisocyanate (MDI) and then the reactive intermediate is subsequently reacted with the pentaerythritol crosslinking initiator.

A second suitable method for synthesizing the PIB-CN material includes using a two-step approach that involves reacting a diisocyanate, as discussed herein, with the cross-linking initiator, such as a polyol or a polyamine as discussed herein, to form a polyisocyanate and reacting the polyisocyanate with a telechelic polyisobutylene derivative to form the PIB-CN material. In particular, in some embodiments, the second method includes (1) reacting the diisocyanate with the polyol or the polyamine to form the polyisocyanate and subsequently (2) reacting the polyisocyanate with a telechelic PIB-diol, as discussed herein, to form the PIB-CN material. For example, a 4,4'-methylenephenyl diisocyanate (MDI) can be reacted first with the polyol 1,1,2,2-Tetrakis(p-hydroxyphenyl)ethane to form the polyisocyanate, prior to reacting the polyisocyanate with PIB-diol. The polyisocyanate can be combined with other types of PIB derivatives to form the PIB-CN material, in some embodiments.

Figure 9B:
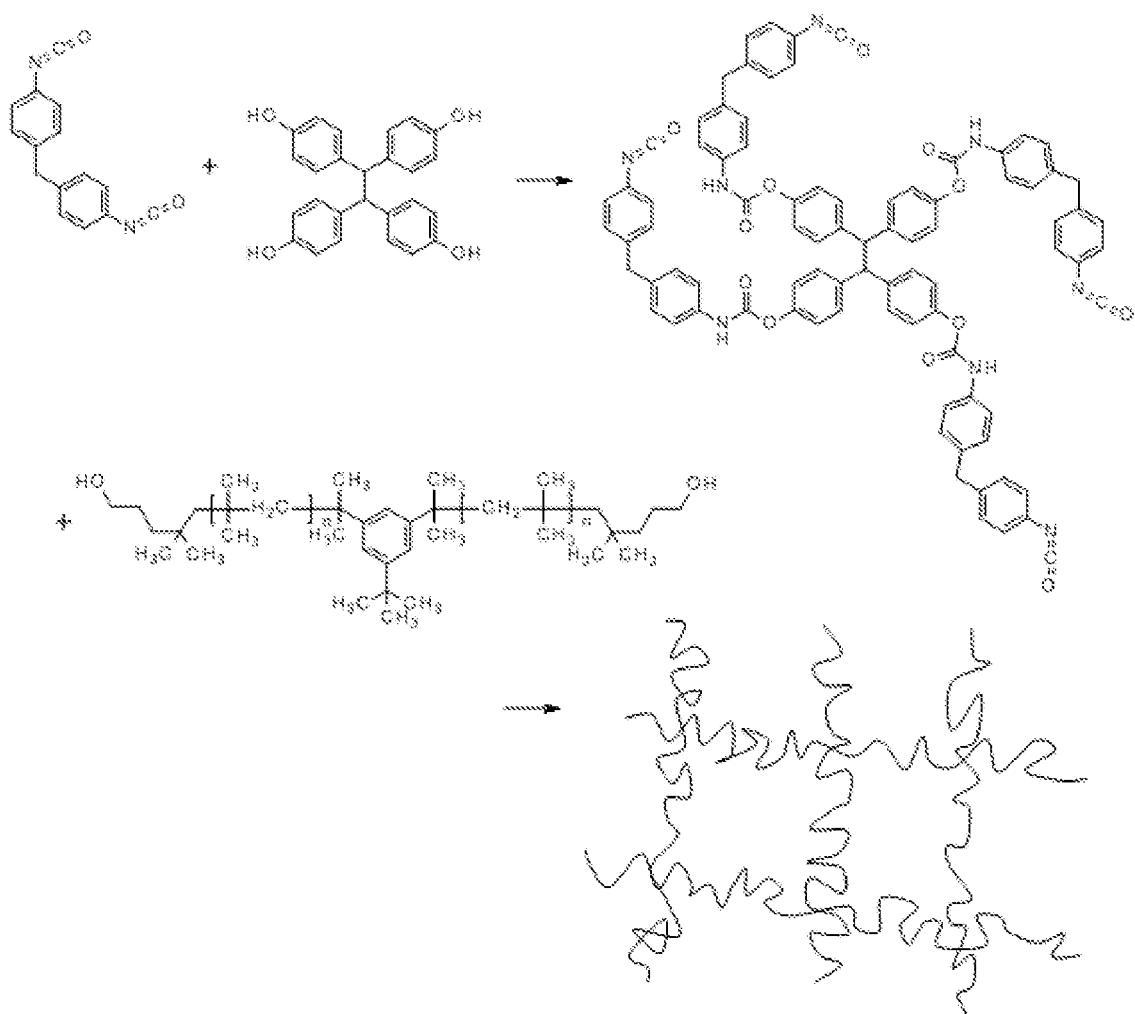
FIG. 9B shows synthesis of PIB-CN material based on a PIB and polyisocyanate reaction.

An exemplary synthetic path for producing the PIB-CN using the second method is provided in FIG. 9B (Scheme 5). As shown in FIG. 9B, two-step synthesis involves reacting a diisocyanate with a polyol or a polyamine and reacting the resulting polyisocyanate with the telechelic polyisobutylene derivative to form the PIB-CN. The synthesis of Scheme 5 specifically shows (1) reacting the diisocyanate with the polyol to form a polyisocyanate and subsequently (2) reacting the polyisocyanate with the telechelic PIB-diol to form the PIB-CN material. More specifically, as shown, the 4,4'-methylenephenyl diisocyanate (MDI) reacts first with the polyol 1,1,2,2-Tetrakis(p-hydroxyphenyl)ethane to form the polyisocyanate, which is then reacted with the FIB-diol to form the PIB-CN.

A third method for synthesizing the PIB-CN material involves converting the telechelic PIB derivative using a Chalk-Harrod hydrosilylation reaction, according to some embodiments. The Chalk-Harrod hydrosilylation reaction involves reacting the telechelic PIB derivative with a silane agent, e.g., phenylsilane, and a transition metal species, e.g., Karstedt's catalyst, to produce the PIB-CN material.

The PIB-CN material can be synthesized by combining the PIB derivative with a transition metal catalyst that is capable of activating vinyl groups of the telechelic PIB derivative to facilitate the formation of crosslink bridges between the PIB derivatives and the silane agents, in some embodiments. Examples of the transition metal catalyst include, but are not limited to, $H_2$ $PtCl_6$, $RhCl_3$, $Rh(PPh_3)_3$ Cl, Ashby's catalyst or Lamoreoux's catalyst, Speier's catalyst, a Karstedt's catalyst, a Wilkinson's catalyst, and a Grubb's first generation catalyst, in some embodiments.

In the Chalk-Harrod hydrosilylation reaction, the PIB derivative may be reacted with the silane agent, which is a crosslinking agent. In some embodiments, the silane agent has more than two reactive hydrosilane groups per molecule in the presence of a catalyst. Described differently, the silane agent has an olefin functionality f that is equal to 2.0 or greater, in some embodiments. The silane agents that may be used in the Chalk-Harrod hydrosilylation reaction include silane agents such as phenylsilane, bishydrosilanes, and trisilanes such as polymethylhydrosiloxane and its copolymers.

Specific examples of silane agents may include diphenyl silane, triphenyl silane, di-l-napthyl silane, phenylsilane, ethyl silane, diethyl silane, triethyl silane, methyl diethyl silane, triisopropyl silane, tri(n-propyl) silane, diphenylmethyl silane, dibenzylsilane, triallyl silane, tri(N-hexyl) silane, tribenzyl silane, trimethyl silane, and tributyl silane. Other examples of silanes include trisilanes that include, but are not limited to, 2,4,6,8-tetramethyl-cyclotetrasiloxane, 1,3,5,7,9,11,13,15-octakis[(dimethylsilyl)oxy]-pentacyclo [9.5.1.13,9.15,15.17,13] octasiloxane, 2,4,6,8,10-pentamethyl-cyclopentasiloxane, 3,3-bis[(dimethylsilyl)oxy]-1,1,5,5-tetramethyl-trisiloxane, 3-[(dimethylsilyl)oxy]-1,1,5,5-tetramethyl-3-phenyl-trisiloxane, 3-[(dimethylsilyl)oxy]-1,1,3,5,5-pentamethyl-trisiloxane, 1,3,5-trisilacyclohexane, 2,4,6,8,10,12-hexamethyl-cyclohexasiloxane, 2,4,6-trimethyl-cyclotrisiloxane, 2,4,6,8-tetraethyl-cyclotetrasiloxane, 3,5-bis[(dimethylsilyl)oxy]-1,1,7,7-tetramethyl-3,5-diphenyl-tetrasiloxane, tris(trimethylsilyl)-germane, 1,2,3,4,5,6-hexamethyl-cyclotrisilazane, tetrakis[3-(dimethylsilyl)propyl]-silane, 2-methyl-, 3-[1,1-bis[(dimethylsilyl)oxy]-3,3-dimethyl-1-disiloxanyl]propyl ester 2-propenoic acid, N,N-bis(dimethylsilyl)-1,1-dimethyl-silanamine, 1,1,3,5,5-pentamethyl-trisiloxane, 3-[(dimethylsilyl)oxy]-1,1,5,5-tetramethyl-3-propyl-trisiloxane, 1,2,4,5-tetrakis(dimethylsilyl)-benzene, 3-[(dimethylsilyl)oxy]-3-ethenyl-1,1,5,5-tetramethyl-trisiloxane, 2,2-bis(dimethylsilyl)-1,1,3,3-tetramethyl-trisilane, 1,2,3,4,5,6,7,8-octamethyl-cyclotetrasilazane, bis[(dimethylsilyl)methyl]methyl-silane, 3-[(dimethylsilyl)oxy]-1,1,5,5-tetramethyl-3-(3,3,3-trifluoropropyl)-trisiloxane, 2-(dimethylsilyl)-1,1,2,3,3-pentamethyl-trisilane, tris[2-(methylsilyl)ethyl]-borane, 3,5-dicyclohexyl-3,5-bis[(dimethylsilyl)oxy]-1,1,7,7-tetramethyl-tetrasiloxane, 3-[(dimethylsilyl)oxy]-3-ethoxy-1,1,5,5-tetramethyl-trisiloxane, 1,1'-silylenebis[2-silyl-benzene, 2,3,5,6-tetrasilyl-2,5-cyclohexadiene-1,4-dione, tris[bis(1,1-dimethylethyl)methylsilyl]-gallium, 2,4,6,8-tetrakis[(dimethylsilyl)oxy]-2,4,6,8-tetraphenyl-cyclotetrasiloxane, (1Z)-1-octen-1-yltris(trimethylsilyl)-germane, 1,3,5,7,9,11,14-heptacyclopentyl-3,7,14-tris[(dimethylsilyl)oxy]-tricyclo [7.3.3.15,11]heptasiloxane, iodotris(trimethylsilyl)-germane, 2,3,6,7,10,11-hexakis(dimethylsilyl)-triphenylene, 3-(2,2-dimethyl-1-phenyldisilanyl)-1,1,1-trimethyl-3-phenyl-disiloxane, 3-[(dimethylsilyl)oxy]-3-ethyl-1,1,5,5-tetramethyl-trisiloxane, 4,6,8-tris [(dimethylsilyl)oxy]-2,4,6,8-tetraphenyl-cyclotetrasiloxan-2-ol, [3-(chloromethylsilyl)propyl]tris[3-(dimethylsilyl) propyl]-silane, N-(chloromethylsilyl)-N-(dimethylsilyl)-1, 1-dimethyl-silanamine, tris(silylmethyl)-silane, 2,2-bis (dimethylsilyl)-1,1,1-triethyl-3,3-dimethyl-trisilane, 2,2-bis (dimethylsilyl)-1,3,3-trimethyl-1,1-diphenyl-trisilane, 2,2-bis(dimethylsilyl)-1,1,3-trimethyl-3-phenyl-trisilane, 2-(dimethylsilyl)-2-ethyl-1,1,3,3-tetramethyl-trisilane, stannanetetrayltetrakis[triphenyl-(9CI) silane, and 2,2,3-tris(dimethylsilyl)-1,1,4,4-tetramethyl-3-(methylphenylsilyl)-tetrasilane.

In some embodiments, the Chalk-Harrod hydrosilylation reaction may include the use of silane agents in conjunction with the difunctional chain extenders, as discussed herein, to modify the distance of cross-linked bonds in the PIB-CN material. In some embodiments, the diisocyanate is 4,4'-methylenephenyl diisocyanate and the chain extender is 1,4-butanediol, as discussed herein.

In some embodiments, an inhibitor may be optionally included in the Chalk-Harrod hydrosilylation reaction (i.e., the third reaction) to control or adjust the reaction rate. A suitable inhibitor is 1-ethynyl-1-cyclohexanol, in some embodiments. Other suitable inhibitors include, but are not limited to, organic materials which contain acetylenic unsaturation and have a boiling point of at least 25° C., such as acetylenic-inhibited platinum-catalyzed organopolysiloxane organic compounds. For example, a suitable inhibitor composition may comprise an organosilicon polymer having an average of from one to three groups per silicon atom selected from the group consisting of monovalent hydrocarbon radicals that are free of acetylenic unsaturation, monovalent halohydrocarbon radicals that are free of acetylenic unsaturation and aliphatic unsaturation, and cyanoalkyl radicals. The organopolysiloxane organic compound can include at least one terminally unsaturated monovalent olefin radical per each molecule, wherein the remaining valences of the silicon atoms of the organosilicon polymer are satisfied by selection from the group consisting of divalent oxygen atoms, divalent hydrocarbon radicals that are free of acetylenic unsaturation, divalent hydrocarbon ether radicals that are free of acetylenic unsaturation, and divalent haloarylene radicals, such that the divalent radicals link the silicon atoms together. The suitable inhibitor composition may also include an organosilicon compound that contains at least one silicon-bonded hydrogen atom per molecule, there being in addition an average of up to two groups per silicon atom selected from the group consisting of monovalent hydrocarbon radicals free of aliphatic unsaturation, monovalent halohydrocarbon radicals free of aliphatic unsaturation, and cyanoalkyl radicals, wherein the remaining valences of the silicon atoms are satisfied by groups selected from the group consisting of divalent oxygen atoms, divalent hydrocarbon radicals free of aliphatic unsaturation, divalent hydrocarbon ether radicals free of aliphatic unsaturation, and divalent haloarylene radicals.

Figure 9C:
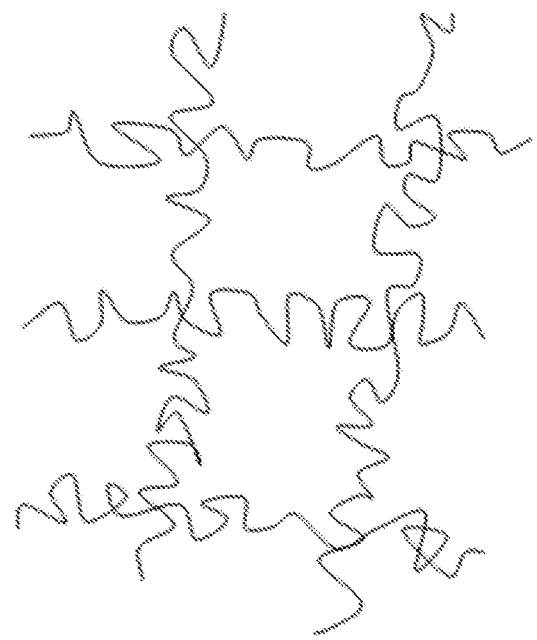
FIG. 9C shows synthesis of PIB-CN material based on a PIB and polyisocyanate reaction.
Figure 9C:
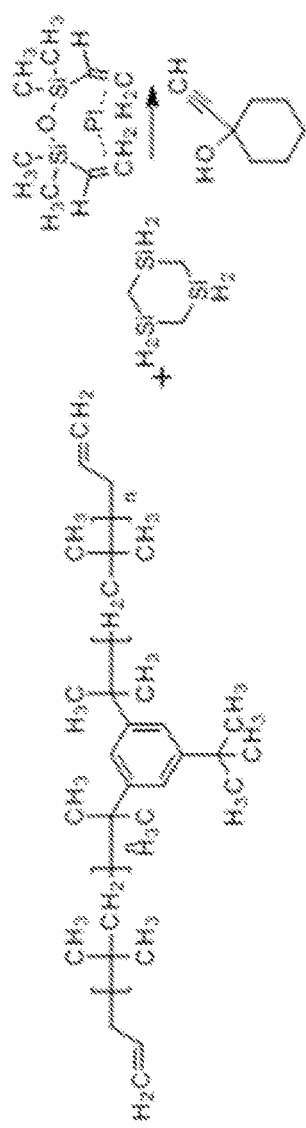

An exemplary Chalk-Harrod hydrosilylation reaction is shown in FIG. 9C (Scheme 6). As shown in FIG. 9C, the telechelic PIB derivative is reacted with the silane agent and the transition metal species to produce the PIB-CN material. In some examples, as shown, the telechelic PIB-allyl is reacted with a phenylsilane and a Karstedt's catalyst to produce the PIB-CN material.

A fourth method for synthesizing the PIB-CN material involves converting the telechelic PIB derivative using a thiol-ene click chemistry reaction, according to some embodiments. A polythiol crosslinking initiators contains more than two reactive thiol groups per molecule. In some embodiments, the telechelic PIB derivative may be reacted with a poly-thiol crosslinking initiator in the presence of a crosslinking initiator to produce a PIB-CN material. In particular, the polythiol crosslinking initiator forms ethyl thioether crosslinks, in some embodiments. Suitable polythiol crosslinking initiators include, but are not limited to, 3-mercapto-1,1'-[2,2-bis[(3-mercapto-1-oxopropoxy) methyl]-1,3-propanediyl] ester propanoic acid, 3-mercapto-1,1'-[2-ethyl-2-[(3-mercapto-1-oxopropoxy)methyl]-1,3-propanediyl] ester propanoic acid, 2-mercapto-1,1'-[2,2-bis[[(2-mercaptoacetyl)oxy]methyl]-1,3-propanediyl]ester acetic acid, 2-mercapto-, 1,1'-[2-ethyl-2-[[(2-mercaptoacetyl)oxy]methyl]-1,3-propanediyl] ester acetic acid, 2,3-bis[(2-mercaptoethyl)thio]-1-propanethiol, 3-mercapto-, 1,1',1''-[(2,4,6-trioxo-1,3,5-triazine-1,3,5(2H,4H,6H)-triyl) tri-2,1-ethanediyl] ester propanoic acid, 1,2,3-propanetrithiol, 3,3'-thiobis[2-[(2-mercaptoethyl)thio]-1-propanethiol, 2,2',2''-nitrilotris-ethanethiol, 2,2-bis(mercaptomethyl)-1,3-propanedithiol, 2-mercapto-, 1,1',1''-(1,2,3-propanetriyl) ester acetic acid, 2-mercapto-, 1,1'-[2-[[(2-mercaptoacetyl) oxy]methyl]-2-methyl-1,3-propanediyl] ester acetic acid, 2-mercapto-, ester with 1,2,6-hexanetriol (3:1) acetic acid, 1,2,4,5-benzenetetramethanethiol, 2,4,6-trichloro-1,3,5-benzenetrimethanethiol, 2,2-bis[(mercaptomethyl)thio]-ethanethiol, 2-[2-mercapto-1-(mercaptomethyl)ethylidene]-hydrazinecarbothioamide.

Figure 9D:
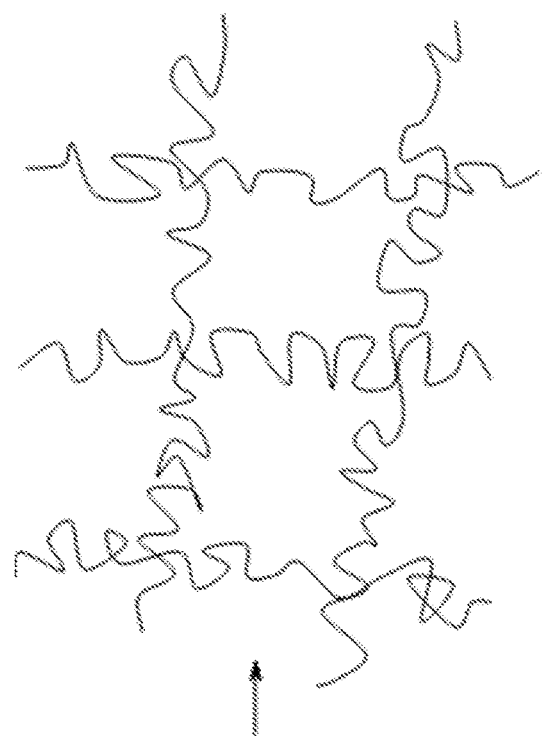
FIG. 9D shows synthesis of PIB-CN material based on a thiol-ene click chemistry reaction.
Figure 9D:
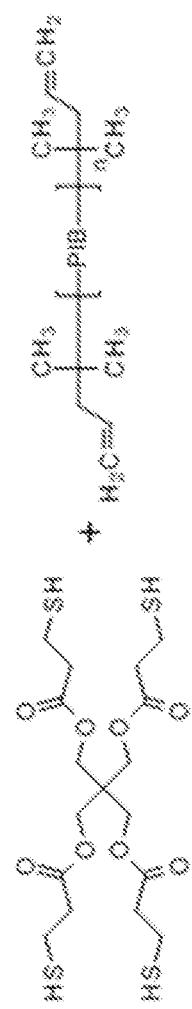

An exemplary reaction is shown in FIG. 9D (Scheme 7). As shown in FIG. 9D, the telechelic PIB derivative may be reacted with the poly-thiol cross linker in the presence of the crosslinking initiator to produce the PIB-CN material.

The PIB-CN material produced by one of the various synthesis methods as discussed herein may be used to construct a PIB-CN seal. In some embodiments, the PIB-CN seal is used as a seal in a medical device. In some embodiments, the feed-thru connector assembly is used as a seal in a feed-thru connector assembly.

Figure 4:
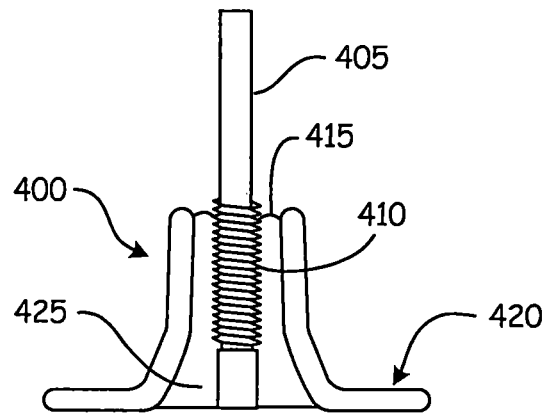
Figure 5:
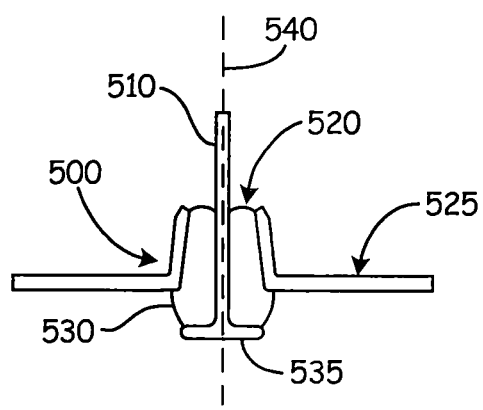
Figure 6:
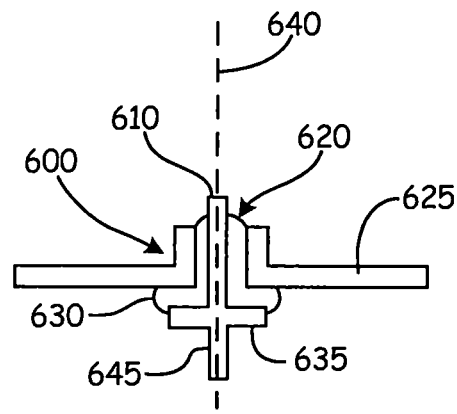

FIGS. 4-6 provide cross-sectional views of feed-thru connector assemblies according to various embodiments. FIG. 4 provides an alternative embodiment of a feed-thru connector assembly 400 of a pulse generator 205 (FIG. 2) that includes a wire 405 having a contoured surface 410 disposed within an opening 415 in a pulse generator housing 420. As shown, the contoured surface 410 is a threaded feature along at least a portion of the wire 405. In various embodiments, the contoured surface 410 of the wire 405 can improve the bonding characteristics between a seal 425 and the wire 405. In some embodiments, at least a portion of the wire 405 includes a textured surface resulting from grit blasting or etching that increases the bond between the wire 405 and the seal 425.

FIG. 5 provides an alternative embodiment of a feed-thru connector assembly 500 of pulse generator 205 (FIG. 2) that includes a wire 510 disposed within an opening 520 of a pulse generator housing 525, wherein one end of the wire 510 includes a head portion 535. In various embodiments, the head portion 535 of the wire 510 may improve bonding characteristics between a seal 530 and the wire 510. In some embodiments, the wire 510 includes the head portion 535 with a flat, cross-sectional geometry orthogonal to a longitudinal axis 540 of the wire 510. The head portion 535 may facilitate bonding between the wire 510 and electronics (FIG. 7) within pulse generator 205 (FIG. 2). The head portion 535 can comprise a variety of cross-sectional geometries. For example, the cross-sectional geometry for the head portion 535 may include a variety of polygonal shapes, in some embodiments. For example, the head portion 535 may include a triangular-shaped head to facilitate a better stability to pitch ratio when connected to the printed circuit board 720 (FIG. 7), in some embodiments.

FIG. 6 provides an alternative embodiment of a feed-thru connector assembly 600 that includes a wire 610 disposed within an opening 620 of a pulse generator housing 625, wherein one end of the wire 610 includes a head portion 635 positioned proximate to the end of the wire 610. As shown, a wire 610 extends along a longitudinal axis 640 in opposite directions from the head portion 635. The wire 610 in FIG. 6 forms an extended portion 645 of the wire 610 at the distal most end of the wire 610. In some embodiments, the extended portion 645 of the wire 610 facilitates direct fixation to a printed circuit board 720 (FIG. 7) or other electronics within the pulse generator 205 (FIG. 2).

The feed-thru connector 600 can include at least one feature that increases a length to area ratio of the formed seal 630. For example, as shown in FIG. 6, the extended portion 645 of the wire 610 can form a volumetric space for the seal 630 between the wire 610 and the pulse generator housing 625. The volumetric space may be configured to provide a higher length to area ratio for the formed seal 630, in some embodiments. A formed seal 630 with the increased length to area ratio can have a larger bonding surface area that improves the bond between the seal 630 and its surrounding components, such as the wire 610 and the pulse generator housing 625.

In some embodiments, the extended portion 645 of the wire 610 is operatively connected to the printed circuit board. In some embodiments, the extended wire 610 is operatively connected to the printed circuit board by a shielding layer.

Figure 7:
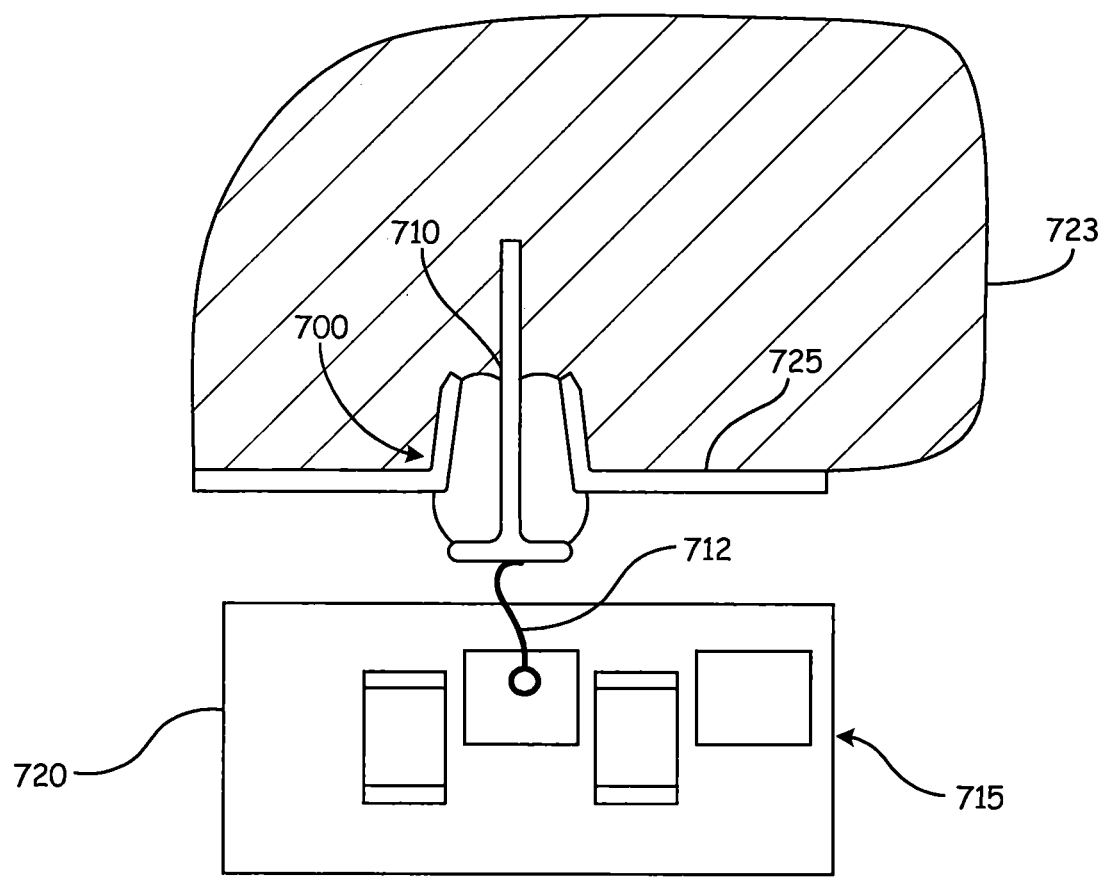
FIG. 7 is a cross-sectional view of an alternative feed-thru structure and its adjacent components according to various embodiments of the invention.

FIG. 7 shows an illustration of an alternative embodiment of a feed-thru connector assembly 700 and components adjacent thereto. As shown, the wire 710 is operatively connected indirectly by a connecting wire 712 to electronics 715, e.g., a printed circuit board 720 or other electronic components, within the pulse generator housing 725. In some embodiments, the wire 710 is operatively connected directly to the electronics 715 within the pulse generator housing 725. In some embodiments, the wire 710 is affixed to the printed circuit board 720 with filler caps to secure the connection therebetween. As shown in FIG. 7, a header 723 is disposed over the feed-thru connector assembly 700.

There are various benefits of using the PIB-CN seal for the feed-thru connector assembly in the pulse generator 205. As discussed herein, the PIB-CN seal possesses vapor-transmission characteristics that are ideal for creating the hermetic seal in the pulse generator 205, in various embodiments. Other beneficial characteristics of the PIB-CN seal may include suitable hydrophobicity, chemical resistance, and electric insulative properties for an electrical implantable device, according to some embodiments. Furthermore, the PIB-CN seal can provide a thermally, oxidatively, and hydrolytically stable seal material.

Method of Creating a Feed-Thru Connector Comprising a PIB-CN Seal

The feed-thru connector of the pulse generator may be constructed using various methods and processes. Non-limiting examples of various methods and processes are provided hereinafter.

Figure 8:
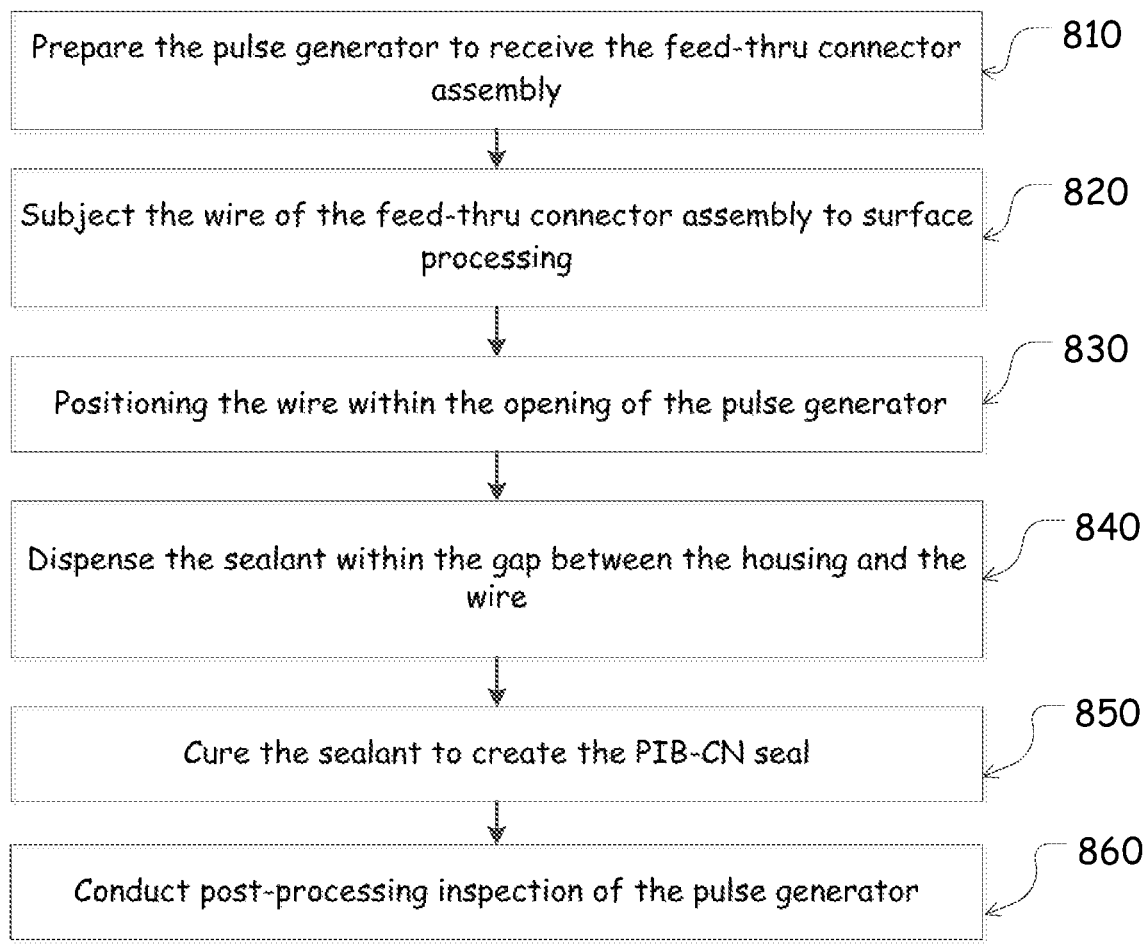
FIG. 8 is flow chart illustrating a method of manufacturing a feed-thru structure according to various embodiments of the invention.

FIG. 8 provides a flow chart illustrating a method 800 of manufacturing feed-thru connector that includes the PIB-CN seal. The method 800 may be used with a pulse generator included with an implantable medical lead system in a number of various applications including, for example, a cardiac rhythm management (CRM) system or a neurostimulation system. The method 800 may be used to create the hermetic seal of the pulse generator having suitable electrical and mechanical properties.

The method 800 optionally includes preparing the pulse generator to receive the feed-thru connector assembly (block 810), according to some embodiments. In some embodiments, preparing the pulse generator housing includes creating the opening in the pulse generator housing. As an alternative option, in some embodiments, the manufacturer may obtain pre-fabricated pulse generators that includes a suitable opening.

In various embodiments, the method 800 optionally includes surface processing of at least a portion of the wire of the feed-thru connector assembly (block 820). The surface processing may include cleaning the surface, activating the surface and priming the surface of the wire.

Cleaning the surface of the wire removes particulates and oils from the edges and surface of the wire. In some embodiments, the wire is cleaned prior to being bonded to the pulse generator housing. Other examples of surface cleaning that can be applied to the wire include, but are not limited to, passivation, etching, polishing, or combinations thereof.

Plasma treating is a surface modification process that uses ionized gas molecules, e.g., argon or oxygen, to alter the surface characteristics of a polymer. Plasma treatment may remove volatile organic compounds from a polymeric material. Also, plasma treatment may be used to activate the surface of a material that does not typically bond easily, or exhibits hydrophobic characteristics. In some embodiments, plasma treating may be used to temporary activate the surface of the wire to improve bonding between the wire and the seal.

Another example of surface processing includes applying a primer on at least a portion of the wire. The primer can promote bonding of the PIB-CN seal to the wire. Various suitable primers, in various embodiments, can be used to facilitate network coupling by promoting covalent bonding between the PIB-CN and the wire. In some embodiments, the surface may be primed with an olefin-functionalized primer. Examples of suitable priming agents include, but are not limited to, isocyanates such as methylene diphenyl diisocyanate (MDI), fluorosilanes, orthosilane esters, and epoxy functional silanes such as Silquest A-174.

The method 800 includes positioning the wire within the opening of the pulse generator (block 830). The wire can be positioned appropriately relative to the opening with the use of a template or positioning fixture. The wire is positioned within the opening such that the longitudinal axis of the wire extends axially through the opening of the housing, in some embodiments. The wire can be oriented such that the proximal end of the wire extends outwardly from the opening and the distal end extends into the interior of the housing, in some embodiments.

The method 800 includes dispensing the sealant in the form of a PIB reactant mixture within the gap between the housing and the wire (block 840), in various embodiments. The "PIB reactant mixture" is a term defining a mixture of two or more reactants from the syntheses that produce the PIB-CN, as discussed herein. The PIB reactant mixture is a combination of the reactants as described herein that can be combined to form a PIB-CN seal.

The sealant is disposed between the wire and portions of the housing adjacent to the wire that define the opening in the pulse generator, in some embodiments. In various embodiments, the sealant has a suitable viscosity that allows the sealant to flow into the opening. The viscosity of the sealant is sufficiently high enough to hold the sealant in place within the gap prior to and during curing, in some embodiments.

Pot life of a material can be an important factor in determining whether the PIB-CN material is suitable for manufacturing. The pot life of a material is the period of time during which a reacting composition remains suitable for its intended processing after the composition is mixed with reaction-initiating agents. The sealant can have a suitable pot life that ranges from about 2 minutes to about 30 mins. In some embodiments, a suitable pot life time period for the sealant ranges from about 2 minutes to about 5 minutes. Other suitable pot life time periods includes from about 2 minutes to about 10 minutes, from about 5 minutes to 15 minutes and from about 15 minutes to 30 minutes, in some embodiments.

The method 800 includes curing the sealant to create the PIB-CN seal (block 850), in some embodiments. The curing process allows the sealant to form the seal within the feed-thru connector assembly, in some embodiments. For example, the PIB reactant mixture such as a mixture comprising the telechelic PIB derivative, as discussed herein, and the poly-thiol crosslinking initiator, as discussed herein, may be cured to form the PIB-CN seal, in some embodiments. In various embodiments, the sealant is cured at atmospheric pressure and at low temperatures. In some embodiments, the sealant may be cured at any temperature or temperature range from about 18° C. (64° F.) to about 200° C. (392° F.). Generally, the sealant may be cured at temperature less than or equal to 100° C. (212° F.). More optimally, sealant can be cured at temperature less than or equal to 70° C. (158° F.), in some embodiments. Other exemplary curing temperatures for the sealant may include a curing temperature less than or equal to 200° C. (392° F.), 100° C. (212° F.), 85° C. (185° F.) or 60° C. (140° F.). The sealant can be cured at a room temperature as well as at an elevated temperature, e.g., above room temperature. In some embodiments, the sealant is cured at a temperature ranging from 18° C. (64° F.) to 23° C. (73° F.), from about 50° C. (122° F.) to about 60° C. (140° F.), from about 50° C. (122° F.) to about 70° C. (158° F.), about 60° C. (140° F.) to about 85° C. (185° F.), and from about 60° C. (140° F.) to about 100° C. (212° F.), in some embodiments.

The method 800 optionally includes post-processing inspection of the pulse generator (block 860), according to some embodiments. The visual inspection, leak testing and electrical testing of the pulse generators can be included in the post-processing inspection. The pulse generator can be visually inspected for manufacturing-related or component-related defects, e.g., a seal delamination or a fractured wire, in some embodiments. The pulse generator can be leak tested to identify defective seals, in some embodiments. The pulse generator can be electrically tested to determine whether the feed-thru assembly has suitable electrical properties for the pulse generator.

The leak testing may include the use of a mass spectrometer leak detector tuned to detect small quantities of helium. The leak test is utilized by pacemaker and pacemaker electronic component manufacturers to test electronic components (integrated circuits, transistors, capacitors, etc.) for hermeticity. For example, there are presently a number of test specifications in use, both military and commercial, for performing helium fine leak detection and gross leak detection. In some embodiments, specifications and testing procedure used for leak testing may include Military Standards 883, 750, and 202 (MIL-STD-883, MIL-STD-750 and MIL-STD-202) and the American Society for Testing and Materials (ASTM) F/34-72T specification. The pulse generator may have a suitable leak test rate that is less than about $4\times10^{-9}$ atmosphere cubic centimeters per second (atm cc/s), or $4\times10^{-9}$ millibars liters per second (mbar L/s), or $4\times10^{-9}$ pascals cubic meters per second (Pa m$^3$/s) when subjected to helium gas at a pressure of about 0.4 pascals (Pa), or $6\times10^{-5}$ psi, in some embodiments. In some embodiments, other suitable leak test rates include a leak rate less than about $2\times10^{-9}$ atm cc/s, about $2\times10^{-9}$ mbar L/s, or about $2\times10^{-9}$ Pa m$^3$/s or about $5\times10^{-9}$ atm cc/s, or $5\times10^{-9}$ mbar L/s, or $5\times10^{-9}$ Pa m$^3$/s, when subjected to helium gas at a pressure of about 0.4 pascals (Pa), or $6\times10^{-5}$ psi. Yet other suitable leak test rates include a leak rate less than about $2\times10^{-10}$ atm cc/s, about $2\times10^{-10}$ mbar L/s, or about $2\times10^{-10}$ Pa m$^3$/s or less than about $5\times10^{-10}$ atm cc/s, or $5\times10^{-10}$ mbar L/s, or $5\times10^{-10}$ Pa m$^3$/s, when subjected to helium gas at a pressure of about 0.4 pascals (Pa), or $6\times10^{-5}$ psi.

The electrical testing may include dielectric strength testing, surface resistivity testing and volume resistivity testing. Dielectric Strength is a measure of the electrical strength of a material as an insulator. Dielectric strength is defined as the maximum voltage required to produce a dielectric breakdown through the material and is expressed as volts per unit thickness. A material with a higher dielectric strength has stronger insulative characteristics.

Dielectric testing is performed by applying a voltage to an electrical component that exceeds its normal operating voltage. The purpose of the test is to determine if a component's insulation is adequate enough to protect the user from electric shock. Dielectric testing is necessary to ensure that the insulating mechanism of an electrical component will withstand voltage variations under normal operating conditions. Dielectric strength testing may be tested in accordance with ASTM D149-09, in some embodiments.

The dielectric strength of the seal is greater than 100 volts per one thousandth of an inch (v/mil), in some embodiments. Suitable dielectric strength values include a dielectric strength value greater than 1,000 v/mil or a dielectric strength range from about 3,000 v/mil to about 5,000 v/mil.

The surface resistivity is the resistance to leakage current along the surface of an insulating material while the volume resistivity is the resistance to leakage current through the body of an insulating material. A higher surface/volume resistivity indicates a lower leakage current and a less conductive material.

In some embodiments, ASTM D257-07 may be used to test for surface and volume resistivity testing. In surface and volume resistivity testing, voltage is applied to a standard size specimen that is placed between two electrodes for sixty seconds and the resistance is measured. The standard size specimen is preferably a 4-inch disk, but may be any practical form, such as flat plates, rods or tubes for insulation resistance. The surface or volume resistivity is calculated in which surface resistivity and volume resistivity may be expressed in ohm·centimeter (ohm-cm) or ohm·meter (ohm-m).

A suitable bulk resistivity of the seal can be greater than $1\times10^6$ ohm-m, in various embodiments. More optimally, a suitable bulk resistivity of the seal is greater than $1\times10^7$ ohm-m, in some embodiments.

A suitable surface resistivity of the seal can be greater than $1\times10^6$ ohm-m, in various embodiments. The surface resistivity of the seal is optimally greater than $1\times10^7$ ohm-m, in some embodiments.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

Example 1

The present invention is more particularly described in the following example, which is intended as illustration only, since numerous modifications and variations within the scope of the present invention will be apparent to those skilled in the art.

Syntheses of Polyisobutylene Cross-Linked Networks (PIB-CN)

Test Samples

Five test PIB-CN samples (PIB-CN-1 through PIB-CN-5) were synthesized by converting a telechelic hydroxyl, propyl terminated PIB-diol to a diisocyanate derivative and subsequently reacting the diisocyanate derivative with a crosslinking initiator to form the PIB-CN samples, as discussed herein and shown in exemplary Scheme 4. Specifically, the five test samples were produced by reacting the PIB-diol with MDI (CAS No. 101-68-8) in a first step to produce the diisocyanate derivative and by reacting the diisocyanate derivative with a crosslinking initiator tris(2-aminoethylamine) or "TAEA" (CAS No. 4097-8906) in a second step at room temperature.

Table 1 provides the weight of the reactants used to produce the test samples.

TABLE 1

| Example | PIB-diol (MW = 2,000 g/mol) weight (g) | MDI (MW = 250.25 g/mol) weight (g) | TAEA (MW = 146.23 g/mol) weight (g) |
|---|---|---|---|
| PIB-CN-1 | 2.01 | 0.2540 | 0.0015 |
| PIB-CN-2 | 2.00 | 0.2578 | 0.0029 |
| PIB-CN-3 | 2.02 | 0.2690 | 0.0073 |
| PIB-CN-4 | 2.00 | 0.2878 | 0.0146 |
| PIB-CN-5 | 2.00 | 0.3441 | 0.0366 |

The first step of the PIB-CN synthesis was carried out by adding a predetermined amount of the PIB-diol and the MDI into a polyethylene mixing cup. The PIB-diol and MDI were speed mixed for about 10 minutes at a mixing rate of 2000 revolutions per minute (rpm) using a Thinky Mixer Model ARE-250.

The second step of the synthesis included adding a tris(2-aminoethylamine) crosslinking initiator to the mixture and speed mixing for about 10 minutes at 2,000 rpm.

Specimen Observations

Five test PIB-CN samples (PIB-CN-1 through PIB-CN-5) were inspected for pot life and for level of curing following the last mixing step. The observations of the samples are provided in Table 2.

TABLE 2

| Example | Pot Life Observations | Curing Observations |
|---|---|---|
| PIB-CN-1 | Cloudy, viscous liquid after 5 minutes | Cloudy, tacky, viscous liquid after 24 hours |
| PIB-CN-2 | Cloudy and gel-like between 2-5 minutes | Clear and tacky gel after 24 hours |

TABLE 2-continued

| Example | Pot Life Observations | Curing Observations |
|---|---|---|
| PIB-CN-3 | Cloudy and gel-like between 2-5 minutes | Clear rubber after 24 hours |
| PIB-CN-4 | Cloudy and gel-like <1 minute | Clear rubber after 24 hours |
| PIB-CN-5 | Cloudy and gel-like <1 minute | Clear rubber after 24 hours |

The pot life assessments included visual and tactile inspections of the samples from 1 minute to 5 minutes following the last mixing step. The tactile observations of the test samples, together with the visual observations, were assessed to determine whether the samples had a pot life that was within a 5-minute time frame.

The pot life of a material is the period of time during which a reacting composition remains suitable for its intended processing after the composition is mixed with reaction-initiating agents. The pot life of a material can be an important factor in determining whether the PIB-CN material is suitable for manufacturing. A pot life time that is too long may be undesirable since material storage and manufacturing throughput time adds to the cost of manufacturing. Alternatively, a pot life time that is too short may also be undesirable since it can cause the sealant to cure prior to being properly positioned on components of a device.

Tactile and visual observations of sample PIB-CN-1 showed that the sample was a cloudy and viscous liquid after 5 minutes, which indicated that the material had a pot life exceeding 5 minutes. Samples PIB-CN-3, PIB-CN-4 and PIB-CN-5 exhibited gel-like tactility within 5 minutes, demonstrating that these materials had sufficiently reacted within 5 minutes and possessed a pot life less than 5 minutes. More specifically, samples PIB-CN-2 through PIB-CN-5 became cloudy but gel-like materials between 2 minutes and 5 minutes, demonstrating that these samples had a suitable pot life for manufacturing. Samples PIB-CN-4 and PIB-CN-5, however, reacted very quickly and had a pot life less than one minute that would likely be unsuitable for manufacturing.

The level of curing assessment included visual and tactile inspections of the samples after 24 hours following the last mixing step. The visual observations of the test samples were assessed to determine whether the test samples had adequately cured as a single phase material after 24 hours. Transparency can be an indicator of whether the material has cured as a single phase material. In contrast, a material that remains as a two-phase material will appear cloudy.

The visual observations of the test samples showed that samples PIB-CN-2 through PIB-CN-5 were clear materials after 24 hours following the second mixing step. Only sample PIB-CN-1 remained cloudy after 24 hours. Accordingly, concentrations of the reactants of samples PIB-CN-2 through PIB-CN-5 appeared to have successfully produced a single phase material within a 24-hour time frame.

The tactile observations of the test samples were also assessed to determine whether the test samples had adequately cured after 24 hours. The tactile observations of sample PIB-CN-1 showed that the material was a tacky, viscous liquid after 24 hours, indicating that the material had not suitably cured.

Sample PIB-CN-2 was a clear but tacky material, demonstrating that the sample had become a single phase material but had not fully cured after 24 hours. Sample PIB-CN-2 was assessed as being potentially useful for producing PIB-CN material even through the cure time was greater than 24 hours since crosslinking initiator, as discussed herein, could have been added to the sample to accelerate the curing process.

Samples PIB-CN-3, PIB-CN-4 and PIB-CN-5 were all clear materials that exhibited rubbery tactility after 24 hours, demonstrating that these materials had sufficiently cured as a single phase material. However, since Samples PIB-CN-4 and PIB-CN-5, had a very short pot life, these samples would likely be unsuitable for manufacturing.

Sample PIB-CN-3 provided the best results when compared to the other test samples. Sample PIB-CN-3 had suitably cured within 24 hours and showed to have a pot life within a 2 to 5 minute timeframe. Accordingly, Sample PIB-CN-3 exhibited the visual and tactile qualities that are desirable for the feed-thru assembly design and feed-thru manufacturing.

We claim:

1. A method of making a feed-thru connector assembly for a pulse generator, the method comprising:
    priming at least a portion of a surface of a conductor with a primer, wherein the primer is a methylene diphenyl diisocyanate (MDI);
    inserting the conductor within an opening within a housing of the pulse generator, the conductor being coupled to electronics housed within the housing;
    dispensing a sealant in a gap between the primed surface of the conductor and portions of the housing adjacent to the conductor that define the opening of the housing; and
    forming a seal comprising a polyisobutylene cross-linked network and adapted to seal between the conductor and the housing;
    wherein the seal is covalently bonded to the conductor;
    wherein forming the seal comprising the polyisobutylene cross-linked network consists of:
        reacting a telechelic polyisobutylene diol and an excess of diisocyanate to form a diisocyanate end-capped polyisobutylene; and
        reacting the diisocyanate end-capped polyisobutylene with a crosslinking initiator to cure the sealant and form the polyisobutylene cross-linked network.

2. The method of claim 1, wherein the seal is a hermetic seal.

3. The method of claim 2, wherein the seal has a leak test rate less than about $4 \times 10^{-9}$ atm cc/sec (or Pa m$^3$/s) when subjected to helium gas at a pressure of about 0.4 Pa.

4. The method of claim 1, further comprising plasma treating at least a portion of the conductor before priming the conductor.

5. The method of claim 1, wherein the priming of the conductor is before inserting the conductor within the opening within the housing of the pulse generator.

6. The method of claim 1, wherein
    the diisocyanate is 4,4'-methylenephenyl diisocyanate (MDI), and the crosslinking initiator is pentaerythritol.

7. The method of claim 1, wherein
    the diisocyanate is 4,4'-methylenephenyl diisocyanate (MDI), and the crosslinking initiator is tris(2-aminoethylamine).

8. A method of making a feed-thru connector assembly for a pulse generator, the method comprising:
    priming at least a portion of a surface of a conductor with a primer, wherein the primer is a methylene diphenyl diisocyanate (MDI);
    inserting the conductor within an opening within a housing of the pulse generator, the conductor being coupled to electronics housed within the housing;
    dispensing a sealant in a gap between the primed surface of the conductor and portions of the housing adjacent to the conductor that define the opening of the housing; and
    forming a seal comprising a polyisobutylene cross-linked network, and adapted to seal between the conductor and the housing;
    wherein the seal is covalently bonded to the conductor;
    wherein forming the seal comprising the polyisobutylene cross-linked network includes:
        reacting a telechelic polyisobutylene diol and an excess of 4,4'-methylenephenyl diisocyanate (MDI) to form a diisocyanate derivative; and
        reacting the diisocyanate derivative with a tris(2-aminoethylamine) to cure the sealant and form the polyisobutylene cross-linked network.

9. The method of claim 8, wherein the seal is a hermetic seal.

10. The method of claim 8, wherein the seal has a leak test rate less than about $4 \times 10^{-9}$ atm cc/sec (or Pa m$^3$/s) when subjected to helium gas at a pressure of about 0.4 Pa.

11. The method of claim 8, further comprising plasma treating at least a portion of the conductor before priming the conductor.

12. The method of claim 8, wherein the priming of the conductor is before inserting the conductor within the opening within the housing of the pulse generator.

* * * * *